(12) United States Patent
Miller et al.

(10) Patent No.: US 7,115,099 B2
(45) Date of Patent: Oct. 3, 2006

(54) METHOD AND APPARATUS FOR DIAGNOSIS OF A MOOD DISORDER OR PREDISPOSITION THEREFOR

(75) Inventors: Steven Mark Miller, Indooroopilly (AU); John Douglas Pettigrew, Taringa (AU)

(73) Assignee: The University of Queensland, St. Lucia (AU)

( * ) Notice: Subject to any disclaimer, the term of this patent is extended or adjusted under 35 U.S.C. 154(b) by 515 days.

(21) Appl. No.: 10/651,516

(22) Filed: Aug. 29, 2003

(65) Prior Publication Data

US 2005/0101877 A1 May 12, 2005

(51) Int. Cl.
*A61B 13/00* (2006.01)

(52) U.S. Cl. .................................... 600/558

(58) Field of Classification Search .............. 600/558, 600/544, 545, 300; 607/45
See application file for complete search history.

(56) References Cited

OTHER PUBLICATIONS

The Ultralradian Rhythm of Alternating Cerebral Hemispheric Activity, D. Shannahoff-Khalsa, Intern. J. Neuroscience, 1993, vol. 70, pp. 285-298.*
A "Sticky" Interhemispheric Switch in Bipolar Disorder?, J.D. Pettigrew, et al, Proc. R. Soc. Lond. B (1998) 265, pp. 2141-2148.*
Independent Hemispheric Attentional Systems Mediate Visual Search in Split-Brain Patients, S.J. Luck, et al, Nature vol. 342, Nov. 30, 1989, pp. 543-545.*
A Hemispheric Switch in Binocular Rivalry?, J.D. Pettigrew, et al, Proc. Aust. Neuroscience Soc, vol. 9, 1998.*
Fluctuation of an Ambiguous Figure in Dementia Praecox and in Manic Depressive Patients, J. McV. Hunt, et al, J. Abnormal and Social Psychology, vol. 28, 1993, pp. 443-452.*
A Neural Theory of Binocular Rivalry, R. Blake, Psychological Review, 1989, vol. 96, No. 1, pp. 145-167.*
Interhemispheric Transfer in the Split Brain: Long-term Status Following Complete Cerebral Commissurotomy, E. Zaidel, 1996, pp. 491-532.*
What is Rivalling during Binocular Rivalry, N.K. Logothetis, et al, Nature, vol. 380, Apr. 18, 1996, pp. 621-624.*

* cited by examiner

*Primary Examiner*—Mark Hindenburg
*Assistant Examiner*—Brian Szmal
(74) *Attorney, Agent, or Firm*—Fulwider Patton LLP

(57) ABSTRACT

A method for diagnosis of a mood disorder or predisposition therefor in a test subject is disclosed. The method includes the steps of determining binocular rivalry rate in the test subject and comparing the binocular rivalry rate with a corresponding reference rivalry rate to diagnose presence or absence of the mood disorder or predisposition therefor. Also disclosed is use of the diagnostic method in genetic linkage studies for the identification of the molecular defect(s) underlying these disorders, and for the identification of compounds which may alleviate such disorders.

28 Claims, 14 Drawing Sheets

METHOD AND APPARATUS FOR DIAGNOSIS OF A MOOD DISORDER OR PREDISPOSITION THEREFOR

FIELD OF THE INVENTION

THIS INVENTION relates generally to mood disorders. In particular, the present invention is concerned with a method and apparatus for diagnosis of a mood disorder, particularly unipolar and/or bipolar mood disorder, or predisposition therefor. The invention also relates to a process of using the diagnostic method to prevent mood disorders, to identify therapeutic compounds for alleviation of mood disorders, and to identify genetic markers associated with such disorders.

BACKGROUND ART

A variety of mood disorders exist which compromise to varying degrees the social integration and quality of life of affected individuals. The major forms of mood disorder include bipolar disorder (manic depression) and unipolar disorders (major depression and unipolar mama). Other wood disorders include dysthymic disorder, cyclothymic disorder, seasonal affective disorder and substance-induced mood disorder.

Bipolar disorder is a common condition with a lifetime prevalence of 1.2% to 1.6% (Weissman et al. 1988, *Psych. Med.* 18:141–153; Kessler et al. 1994, *Arch Gen. Psych.* 51:8–19). It is characterised by recurrent episodes of mania and depression with symptomatic recovery between episodes.

The pathophysiology of bipolar disorder remains poorly understood despite considerable research (Goodwin et al. 1998, *Arch. Gen. Psych.* 55:23–25). Although it is strongly heritable, the genetics are complex, with less than fill concordance in monozygotic twins (Mitchell et al. 1993, *Aust. & New Zeal. J. Psych.* 27:560–580). At least four different susceptibility loci have been identified (Adams et al. 1998, *Am. J. Hum. Genet;* 62:10841091). A trait-dependent biological marker would assist genetic linkage studies (which are dependent upon the identification of the clinical phenotype) and would potentially lead to an understanding of the underlying molecular defect in bipolar disorder.

In unipolar depression, there are recurrent episodes of depression with symptomatic recovery, but there are no episodes of mania. In unipolar mania there are recurrent episodes of mania but no episodes of depression. Like bipolar disorder, the pathophysiology and specific genetic defects underlying unipolar disorders remain poorly understood.

Current techniques for diagnosing mood disorders rely entirely on subjective interpretation of a patient's condition based on clinical interview. However, apart from being relatively time-consuming, the subjective nature of this technique in interpreting a psychiatric profile does not provide consistently accurate determinations of clinical phenotype. Consequently, misdiagnosis of mood disorders may occur which can thereby affect the prescribed pharmacological and non-pharmacological therapy.

In the 1930s, Hunt and Guilford (1933, *J. Abnormal and Social Psychology* 28:443–452) found that hospitalised manic-depressive patients displayed slow alternation rates when viewing an ambiguous figure (ie. Wheatstone cube) compared to normal controls. The mean passive viewing number of alterations per minute was 4.25 for manic-depressives and 18.06 for normal controls. A strong implication from this study is that such slower alternation rates may be the result of clinical progression. Moreover, the data from this study support the use of this test to confirm the presence of manic-depressive illness in hospitalised individuals with a life history of illness at least as long as that for the individuals in the study.

SUMMARY OF THE INVENTION

The present invention arises from the unexpected discovery of differential rates of binocular rivalry between subjects with mood disorders (particularly unipolar and bipolar mood disorders), and non-clinical controls. In this respect, it was found that euthymic subjects affected by these mood disorders have a statistically significant slower rate of rivalry compared to non-clinical control. Surprisingly, the inventors also discovered that slow rates of binocular rivalry are present in some relatives of subjects with mood disorders. These findings suggest that slow binocular rivalry alternation rate is an alternative phenotypic expression of the bipolar and/or unipolar genotype and is not the result of one or more clinical episodes.

The inventors have also found from unilateral caloric, and transcranial magnetic, stimulation during binocular rivalry (as hereinafter described) that binocular rivalry is likely to be an interhemispheric switching phenomenon, ie. the perceptual alternations relate to alternating activation of the left and right hemispheres of the brain. Thus, the inventors consider that slow binocular rivalry is likely to correspond to slow rate of interhemispheric switching. The inventors have also shown that unilateral caloric stimulation also alters the perceptual alternations of the Necker cube, thus supporting interhemispheric switching as the neural mechanism of ambiguous figures. The similarly abnormal (slow) alternation rates in binocular rivalry and the Necker cube in subjects with bipolar disorder suggest that these perceptual phenomena share a common neural mechanism. The similar effects of caloric stimulation on binocular rivalry and Necker cube alternations suggest that this common neural mechanism is interhemispheric switching.

Accordingly, the inventors have devised a method of diagnosing mood disorders or predisposition therefor based on the above candidate trait-dependent biological marker. The current method therefore may also have utility in genetic linkage studies for the identification of the molecular defect(s) underlying these disorders, and for the identification of compounds which may alleviate such disorders. Other aspects of the invention will become apparent from the following description.

Thus, in one aspect, the invention broadly resides in a method for diagnosis of a mood disorder or predisposition therefor in a test subject, said method including the steps of:
(a) determining an interhemispheric switch rate of the test subject, wherein the test subject has not been diagnosed previously with the mood disorder; and
(b) comparing the switch rate with a corresponding reference switch rate to diagnose presence or absence of the mood disorder or predisposition therefor.

Suitably, the test subject has had less than two episodes of the disorder or is asymptomatic.

Preferably, the interhemispheric switch rate is determined by measuring a rate of perceptual rivalry in the test subject.

The rate of perceptual rivalry may be determined by measuring a rate of reversal of perspective for ambiguous optical stimuli.

Preferably, the rate of perceptual rivalry is determined by measuring a rate of binocular rivalry.

Alternatively, the interhemispheric switch rate may be determined by measuring a rate of the nasal cycle.

Suitably, the rate of perceptual rivalry is measured by:
(a) displaying at least one image to the test subject, wherein the at least one image invokes perceptual alternation;
(b) signalling respective incidences of perceptual alternation in the test subject during a predetermined period to provide a number of signals; and
(c) dividing the number of signals by the predetermined period to provide the rate of perceptual rivalry.

Preferably, the method is characterised in that said signalling is effected by the test subject or by a suitable detection means.

Preferably, the method is further characterised by the step of processing each of the signals relating to interhemispheric alternation to convert these signals into digitised signals, and storing the digitised signals for subsequent use.

Suitably, presence of the mood disorder is diagnosed, or a predisposition therefor is suggested, when the interhemispheric switch rate of the subject is equal to a corresponding reference switch rate associated with the mood disorder or predisposition therefor. In contrast, absence of the mood disorder may be diagnosed, or predisposition therefor discounted, if the above criteria are not satisfied and/or when the interhemispheric switch rate of the subject is equal to a corresponding reference switch rate associated with normal or control phenotype.

In the case of an interhemispheric switch rate determined by binocular rivalry, presence of bipolar disorder is diagnosed, or a predisposition therefor is suggested, preferably when the rate of perceptual alternation in the subject is less than 0.40 Hz, more preferably less than 0.35, and most preferably less than 0.30. Preferably, the stimulus for binocular rivalry is moving gratings.

Conversely, absence of bipolar disorder may be diagnosed, or a predisposition therefor discounted, when the rate of perceptual alternation is greater than 0.35 Hz, more preferably greater than 0.40 Hz, and most preferably greater than 0.45 Hz. Preferably, the stimulus for binocular rivalry is moving gratings.

Suitably, presence of unipolar disorder is diagnosed, or a predisposition therefor suggested, when the rate of perceptual alternation in the subject is in the range of between 0.25 Hz and 0.45 Hz. Preferably, the stimulus for binocular rivalry is moving gratings.

In another aspect, the invention provides a method for diagnosis of a mood disorder or predisposition therefor in a test subject, said method including the steps of:
(a) determining an interhemispheric switch rate of the test subject; and
(b) comparing the switch rate with a corresponding reference switch rate to diagnose presence or absence of the mood disorder or predisposition therefor; wherein the interhemispheric switch rate is not determined by reversal of perspective of ambiguous optical stimuli.

In yet another aspect of the invention, there is provided a method for diagnosis of a mood disorder in a test subject, said method including the steps of:
(a) determining binocular rivalry rate in the subject; and
(b) comparing said rivalry rate with a corresponding reference rivalry rate to diagnose presence or absence of the mood disorder or predisposition therefor.

In still yet another aspect, the invention provides a method for assessing the clinical state of a test subject with a mood disorder, said method including the step of comparing measurements of current relative hemispheric activation to corresponding measurements obtained when said subject was euthymic to thereby ascertain the clinical state.

Preferably, the relative hemi sphere activation is measured by:
(a) recording binocular rivalry in the test subject;
(b) calculating a ratio of total time spent perceiving left eye's presented image versus right eye's presented image;
(c) determining which eye's presented image is represented in which hemisphere; and
(d) interpreting which hemisphere has greater relative activation from the results of the aforementioned steps.

Suitably, the step of determining which eye's presented image is represented in which hemisphere is carried out by the steps of:
(a) stimulating one of said hemispheres;
(b) calculating a post-stimulation ratio of total time spent perceiving left versus right eye's presented image; and
(c) comparing pre- and post-stimulation ratios to determine whether left eye's image or right eye's image is represented in said stimulated or opposite hemisphere.

Suitably, said stimulation is effected by unilateral caloric vestibular and/or unilateral transcranial magnetic stimulation as, for example, hereinafter described.

In a further aspect of the invention, there is provided an apparatus for diagnosing mood disorder, said apparatus comprising:
(a) a monitoring means for monitoring interhemispheric switching in a test subject; and
(b) processing means for determining an interhemispheric switch rate and for comparing said switch rate with a predetermined data set for providing diagnosis of presence or absence of the mood disorder or predisposition therefor.

The monitoring means suitably comprises means for presenting different viewing images separately to each eye and recordal means for recording when the subject perceives a change in the viewed image.

Suitably the different viewing images comprise a moving horizontal grating presented to one eye and a moving vertical grating presented to the other eye. Alternatively, the different viewing images may be a stationary horizontal grating presented to one eye and a stationary vertical grating presented to the other eye.

The monitoring means preferably incorporates a liquid crystal shutter before each eye.

The recordal means for recording perceived change may suitably be a subjective device in the form of an indicator means activated by the test subject when a change is perceived.

Preferably, the recordal means is an objective device that records eye movements as an indicator of which image is being perceived. Alternatively, steady state visual evoked potentials may be measured to provide an objective indication of the perceptual alternation.

The processing means suitably includes timing means and means for receiving signals from the recordal means indicative of perceptual change.

The apparatus may also include change means for inducing a change in ratio of total time spent perceiving left eye's presented image versus right eye's presented image.

In yet a further aspect of the invention there is provided a process for identifying one or more genetic markers associated with a mood disorder, said process including the steps of:
(a) testing respective members of one or more pedigrees affected by the mood disorder using the method of the invention;

(b) identifying members having the mood disorder or predisposition therefor; and
(c) conducting genetic linkage analysis on the identified members to identify the or each genetic marker associated with the mood disorder.

Preferably, the mood disorder is bipolar disorder or unipolar disorder.

In a still yet a further aspect, the invention provides a method of treating a patient with unipolar disorder, said method comprising the steps of:
(a) determining an interhemispheric switch rate of the patient;
(b) comparing said interhemispheric switch rate with a range of reference interhemispheric switch rates associated with bipolar disorder, and
(c) administering to said patient a pharmacologically-effective dosage of a mood-stabilising drug when said interhemispheric switch rate is in said range.

Suitably, the mood stabilising drug is lithium.

Preferably, the interhemispheric switch rate is determined by perceptual alternation more preferably binocular rivalry. In the latter case, the drug is administered to the patient when the alternation rate is below 0.25 Hz, more preferably below 0.20 Hz, and most preferably below 0.15 Hz.

BRIEF DESCRIPTION OF THE DRAWINGS

In order that the invention may be readily understood and put into practical effect, preferred embodiments of the invention will be described with reference to the attached drawings, in which.

DETAILED DESCRIPTION

1. Definitions

Figure 1:
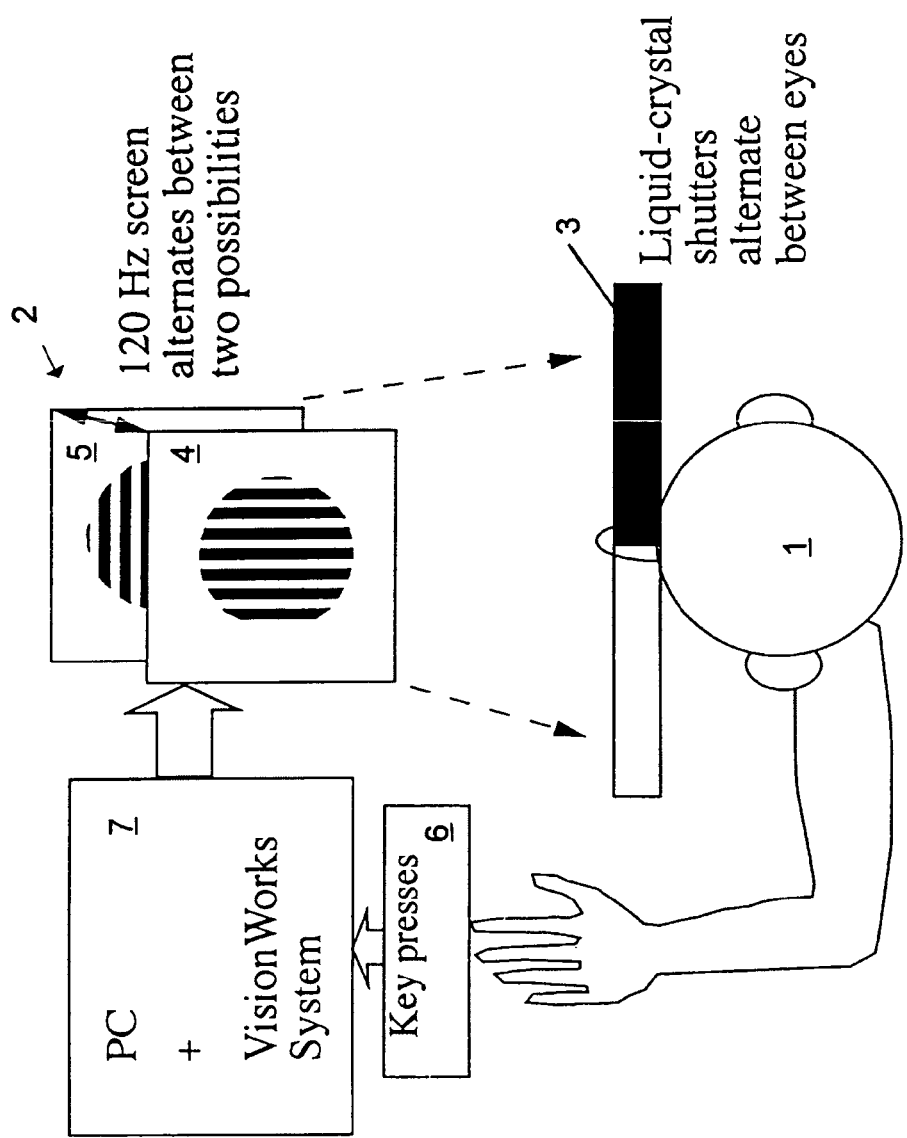
FIG. 1 is one embodiment of a diagnostic apparatus according to the invention. Psychophysical set-up used to examine binocular rivalry. To avoid problems with binocular fixation and alignment, the rivalrous stimuli are presented at the same location. By alternating rapidly between the rivalrous stimuli in phase with liquid crystal shutters, each eye's view can be restricted to the stimulus intended for it. The subject reports the perceived stimulus by depressing one of three keys for horizontal, vertical, or nixed/indeterminate percepts.

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

By "ambiguous optical stimuli" is meant those stimuli able to elicit different perceptions which alternate during continued observations of the same stimulus. Suitable ambiguous stimuli of this type include ambiguous figures such as the Necker cube and Schröder staircase.

The term "binocular rivalry" refers to the alternating perceptual states that arise when viewing different images, presented separately to each eye, in the same retinal location. In this regard, it is well known that when corresponding regions of the two eyes are stimulated by sufficiently different patterns, the stimuli rival in terms of conscious perception, rather than fuse into a composite pattern. Accordingly, a perceptual alternation or switch between these nonfusible dichoptic stimuli results.

The term "genetic marker" includes within its scope a region of a chromosome, locus, allele or fragment thereof that is associated with a particular phenotype.

By "interhemispheric switch rate" is meant the rate of interhemispheric alternation in one or more regions of the brain inclusive of temporo-parietal cortex, hypothalamus, prefrontal and limbic regions of the brain. Preferably, the interhemispheric switch rate relates to the rate of interhemispheric alternation of the temporo-parietal cortex.

Throughout this specification, unless the context requires otherwise, the words "comprise", "comprises" and "comprising" will be understood to imply the inclusion of a stated integer or group of integers but not the exclusion of any other integer or group of integers.

2. Diagnosis of Mood Disorders using Interhemispheric Switch Rates

The present invention arises from the unexpected discovery that the rate of perceptual alternation in binocular rivalry is slow in euthymic subjects with mood disorders, particularly those with bipolar or unipolar disorders. Surprisingly, the inventors also discovered that slow rates of binocular rivalry are present in relatives of subjects with mood disorders. These finding suggests that slow binocular rivalry alternation rate is an alternative phenotypic expression of the bipolar and/or unipolar genotype and is not the result of one or more clinical episodes.

As will be more fully described hereinafter, it has also been found unexpectedly, from two unilateral hemispheric activation techniques in human subjects, that perceptual alternations result from competition between rather than within the cerebral hemispheres. Accordingly, the inventors have proposed an interhemispheric switching mechanism for these perceptual phenomena. It is believed that the interhemispheric switch rate provides a trait-dependent biological marker for mood disorders and in particular, bipolar disorder and unipolar disorder.

From the foregoing, the inventors have devised a method of diagnosing mood disorders or predisposition therefor based on the above candidate trait-dependent biological marker. The method includes the steps of determining an interhemispheric switch rate of the test subject, and comparing the switch rate with a corresponding reference switch rate to diagnose presence or absence of the mood disorder or predisposition therefor. In this regard, the invention broadly encompasses diagnosing a mood disorder or predisposition therefor when the interhemispheric switch rate is aberrant relative to a normal range of interhemispheric switch rates.

The interhemispheric switch rate of the subject may be determined by any suitable technique and, in this regard, techniques that indirectly measure a particular interhemispheric switch rate are also contemplated by the invention. For example, an interhemispheric switch rate relating to the temporo-parietal cortex may be determined by measuring the rate of perceptual rivalry (or perceptual alternation) in the subject. Alternatively, an interhemispheric switch rate relating to hypothalamic activity may be determined by measuring the rate of alternating sympathetic and parasympathetic activity in the nasal turbinates, also known as the nasal cycle (Shannahoff-Khalsa, 1993, *Intern. J. Neuroscience* 70:285–298, which is incorporated herein by reference).

Preferably, the step of determining interhemispheric switch rate is characterised by subjecting the test subject to a stimulus which invokes interhemispheric alternation therein. Any suitable stimulus having such characteristics is contemplated by the invention and in this regard, the stimulus may comprise images that are sufficiently different that rivalry is induced rather than fusion, ie, perceptual rivalry is induced.

The rate of perceptual rivalry may be determined by measuring the rate of reversal of perspective for ambiguous optical stimuli. Exemplary methods which may be used to measure the rate of reversal of perspective include, but are not limited to, those disclosed in George (1935, *J. Gen. Psychol.* 39–59), Washburn and Manning (1933, In *Studies from the psychological laboratory of Vassar College* 632–633), Washburn et al (1933, ibid 633–636), Washburn et al (1933, ibid 636–637), and Borsellino et al (1972, 10.Bd. Heft 3:139–144), which are incorporated herein by reference.

Preferably, the rate of perceptual rivalry is determined by measuring the rate of binocular rivalry. Examples of binocular rivalry techniques include, but are not limited to, those disclosed in Howard and Rogers (1995, "Binocular fusion and rivalry", In *Binocular Fusion and Stereopsis*, eds Mackintosh et al, Oxford University Press), Logothetis et al (1996, *Nature* 380:621–624), Kovacs et al (1996, *Proc. Natl. Acad. Sci. USA*. 93:15508–15511), Sheinberg, and Logothetis (1997, *Proc. Natl. Acad. Sci. USA* 94:3408–3413), and Andrews and Purves (1997, *Proc. Natl. Acad. Sci. USA* 94:9905–9908), which are incorporated herein by reference.

Suitably, the rate of perceptual rivalry is measured by displaying an image to the test subject which image invokes perceptual alternation, signalling respective incidences of perceptual alternation in the test subject during a predetermined period to provide a number of signals and dividing the number of signals by the predetermined period to provide the rate of perceptual rivalry.

Preferably, the method is characterised in that said signalling is effected by the test subject or by a suitable detection means. In the case of a subject effecting the signalling, the subject preferably signals a perceptual alternation or switch. In this context, the subject may signal visually, audibly, or by touch wherein the signal is registrable by a suitable sensor. For example, the subject may depress a button that is suitably operably connected to a signal registration means that registers the signal.

Alternatively, a perceptual alternation may be signalled by a suitable detection means. For example, the detection means may be adapted to measure visually evoked potentials (VEP). In this regard, reference may be made for example, to Brown and Norcia (1997, *Visions Res.* 37:2401–2408, which is incorporated herein by reference) which teach a real-time, steady-state VEP based on labelling each eye's image with a slightly different temporal frequency so that the record generated by each can be recovered by an electroencephalogram (EEG) by spectrum analysis. In this way, it is possible to track the "waxing" and "waning" of the VEP amplitudes for each eye's image simultaneously during spontaneous rivalry, permitting an analysis of the relative dominance of each eye's image in real-time and to determine alternation rate.

Alternatively, the detection means may be adapted to monitor eye movement. For example, Blackwood et al (1996, *Br. J. Psych.* 168:85–92, incorporated herein by reference) teach a smooth-pursuit eye tracking procedure in which a subject visually tacks an image and an electrooculograph is recorded in the horizontal plane via electrodes attached adjacent to the outer canthus of each eye. Reference also may be made to Sweeney et al (1998, *Biol. Psychiatry* 43:584–594, incorporated herein by reference) who disclose the use of infrared recordings to monitor eye movements. Such procedures that monitor eye movements have particular utility in binocular rivalry methods that rely on moving dichoptic stimuli, such as moving vertical and horizontal gratings.

Alternatively, the interhemispheric switch rate may relate to the rate of interhemispheric alternation of hypothalamic activity as mentioned above. Such rate may be determined by measuring the rate of alternating sympathetic and parasympathetic activity in the nasal turbinates, otherwise known as the nasal cycle, as for example disclosed in Shannahoff-Khalsa (1993, supra) and Werntz et al (1983, *Human Neurobiol.* 2:39–43, which is incorporated herein by reference).

Alternating cerebral hemisphere activation may be determined by EEG recordings as for example disclosed in Shannahoff-Khalsa (1993, supra) and Werntz et al (1983, supra).

Also contemplated, as a measure of interhemispheric switch rate is alternation of performance in hemisphere specific functions such as verbal and spatial abilities (Shannahoff-Khalsa, 1993, supra; Klein and Armitage, 1979, *Science* 204:1326–1328, incorporated herein by reference).

Suitably, the method is further characterised by the step of processing each of the signals relating to interhemispheric alternation to convert these signals into digitised signals, and storing the digitised signals for subsequent use.

In preference, the step of determining the rate of interhemispheric switching is further characterised by dividing the number of signals corresponding to interhemispheric alternation by the total time the subject is under test. For example, in the case of perceptual rivalry referred to above, the interhemispheric switch rate may be calculated by dividing the number of perceptual switches by the total time of rivalry. Preferably, in the case of binocular rivalry such calculation excludes mixed or indeterminate percepts.

The step of determining interhemispheric switch rate may further include a practice period wherein the subject becomes familiarised with the test. Suitably, this period is not taken into account when determining the rate of interhemispheric switching.

Suitably, presence of the mood disorder is diagnosed, or a predisposition therefor is suggested, when the interhemispheric switch rate of the subject is equal to a corresponding reference switch rate associated with the mood disorder. In such a case, the corresponding reference switch rate may correspond to a predetermined average range of interhemispheric switch rates in subjects having the mood disorder. In contrast, absence of the mood disorder may be diagnosed, or predisposition therefor discounted, if the above criteria are not satisfied and/or when the interhemispheric switch rate of the subject is equal to a corresponding reference switch rate associated with normal or control phenotype. In such a case, the corresponding reference switch rate may correspond to a predetermined average range of interhemispheric switch rates in non-clinical control subjects.

In the case of an interhemispheric switch rate determined by binocular rivalry, presence of bipolar disorder is diagnosed, or a predisposition therefor is suggested, preferably when the rate of perceptual alternation in the subject is less than 0.40 Hz, more preferably less than 0.35, most preferably less than 0.30. In this regard, a predisposition for bipolar disorder is suggested suitably when the rate of perceptual alternation in a relative of a bipolar subject is less than 0.40 Hz, more preferably less than 0.35, most preferably less than 0.30.

Conversely, absence of bipolar disorder may be diagnosed, or a predisposition therefor discounted, when the rate of perceptual alternation is greater than 0.35 Hz, more preferably greater than 0.40 Hz, and most preferably greater than 0.45 Hz.

Suitably, presence of unipolar disorder is diagnosed, or a predisposition therefor suggested, when the rate of perceptual alternation in the subject is in the range of between 0.25 Hz and 0.45 Hz.

For the above diagnoses or predispositions, the stimulus which invokes binocular rivalry in the test subject preferably comprises moving gratings.

The method may further include the step of repeating the method on at least one separate occasion to validate the diagnosis. In this regard, the subject tested is suitably euthymic.

3. Assessing Clinical State of a Subject with a Mood Disorder

The invention also contemplates a method for assessing the clinical state of a subject with a mood disorder including the step of comparing measurements of current relative hemispheric activation to corresponding measurements obtained when said subject was euthymic to thereby ascertain the clinical state. In this regard, it will be appreciated that mood shifts seen in bipolar disorder are associated with relative hemisphere activation: left hemisphere activation being associated with mania, while right hemisphere activation is associated with depression.

Preferably, the relative hemispheric activation is measured by recording binocular rivalry in the subject calculating a ratio of total time spent perceiving left eye's presented image versus right eye's presented image, determining which eye's presented image is represented in which hemisphere; and interpreting which hemisphere has greater relative activation from the results of the aforementioned steps.

Suitably, the step of determining which eye's presented image is represented in which hemisphere is carried out by the steps of stimulating one of said hemispheres, calculating a post-stimulation ratio of total time spent perceiving left eye's presented image versus right eye's presented age; and comparing pre- and post-stimulation ratios to determine whether left or right eye's image is represented in said stimulated or opposite hemisphere. Preferably, said stimulation is effected by unilateral caloric vestibular and/or unilateral transcranial magnetic stimulation as, for example, hereinafter described.

Alternative methods of measuring relative hemispheric activation may be effected by indirect measures of other interhemispheric switching phenomena such as the nasal cycle and higher functions such as verbal and spatial abilities.

4. Apparatus for Diagnosis of Mood Disorders

The invention also provides an apparatus for diagnosing mood disorder, comprising a monitoring means for monitoring interhemispheric switching in a test subject, and processing means for determining an interhemispheric switch rate and for comparing said switch rate with a predetermined data set for providing diagnosis of presence or absence of the mood disorder or predisposition therefor.

The monitoring means suitably comprises means for presenting different viewing images separately to each eye and recordal means for recording when the subject perceives a change in the viewed image.

Suitably the different viewing images are a moving horizontal grating presented to one eye and a moving vertical grating presented to the other eye. Alternatively, the different viewing images comprise a stationary horizontal grating presented to one eye and a stationary vertical grating presented to the other eye. Other visually distinct images, such as mentioned in the prior art relating to binocular rivalry, can also be employed.

The monitoring means preferably incorporates a liquid crystal shutter before each eye. The liquid crystal shutters allow the field of view of each eye to be superimposed so that the different viewing images are presented at the same retinal location.

The recordal means for recording perceived change is suitably a subjective device in the form of an indicator means activated by the test subject when a change is perceived. Preferably, the recordal means is an objective device that records eye movements as an indicator of which image is being perceived. Alternatively, steady state visual evoked potentials may be measured to provide an objective indication of the perceptual alternation.

The processing means suitably includes timing means and means for receiving signals from the recordal means indicative of perceptual change. Interhemispheric switch rate is calculated by dividing the number of perceptual switches by the total time of perceptual rivalry.

The apparatus may also include change means for inducing a change in ratio of total time spent perceiving left eye's presented image versus right eye's presented image. The change means may be a caloric vestibular stimulation means, trans-cranial magnetic stimulation means, contrast altering means, or other means known to produce a change in the interhemispheric switch rate.

5. Use of Diagnostic Method to Identify Genetic Markers Linked to Mood Disorders Also contemplated is a process for identifying one or more genetic markers associated with a mood disorder, including the steps of testing respective members of one or more pedigrees affected by the mood disorder using the method of the invention, identifying members having the mood disorder or predisposition therefor; and conducting genetic linkage analysis on the identified members to identify the or each genetic marker associated with the mood disorder.

Linkage analysis is well known to those of skill in the art. Exemplary protocols which may be used for this purpose include, but are not limited to, those disclosed in Dracopoli et al (1994, "*Current Protocols in Human Genetics*", John Wiley and Sons Inc., USA), Ott, J. (1991, "*Analysis of Human Genetic Linkage*" Johns Hopkins University Press), and Adams et al. (1998, *Am. J. Hum. Genet.* 62:1084–1091), which are incorporated herein by reference.

The invention also contemplates linkage studies carried out on non-affected individuals ie. non-pedigree members. In this regard, one subset of the non-affected individuals will have fast interhemispheric switch rates and another subset will have slow interhemispheric switch rates. The application of linkage analysis to these subsets will be advantageous in identifying molecular markers linked to switch rate (a quantitatively varying trait). These markers may then be employed for the identification of molecular markers linked to mood disorders such as bipolar disorder and unipolar disorder.

The invention also extends to the genetic marker(s) obtained by the aforementioned process.

6. Use of Diagnostic Method to Identify Candidate Therapeutic Agents

The invention also provides a process for identifying a candidate therapeutic agent for alleviating a mood disorder, including the steps of measuring fiat interhemispheric switch rate in a test specimen, administering or applying a test compound to said test specimen, measuring second interhemispheric switch rate in the test specimen, and identifying a candidate therapeutic agent if said second interhemispheric switch rate is faster than said first interhemispheric switch rate. Suitably, the test specimen includes, but is not limited to, a human, an animal, brain tissue thereof or brain cell(s) thereof.

Any suitable method may be used to determine interhemispheric switch rate. For example, methods hereinbefore described may be used in the case when the test specimen is a human or animal. Alternatively, when the test specimen is an animal, electrical activity of brainstem or hypothalamic neurones associated with interhemispheric switching may be measured. This particular technique may also be used when the test specimen is brain tissue or brain cells. An example of a method which uses such measurement of electrical activity in vitro and/or in vivo is described by Schaap et al (1997, *Brain Res.* 753:322–327) which is incorporated herein by reference.

Alternatively, interhemispheric switch rate may be determined by inducing, in the test specimen, spontaneous nystagmus that alternates in direction (periodic alternating nystagmus (PAN)). In this regard, reference may be made to methods of inducing PAN respectively in humans (Baloh et al., 1976, *Brain* 99:11–26), monkeys (Waespe et al., 1984, *Science* 228:199–202) and goldfish (Dow and Anastasio, 1997, *NeuoReport* 8:2755–2759), which methods are incorporated herein by reference. In PAN, the cycle length of the alternating eye movements is known to vary (Baloh et al., supra). Accordingly, the period of alternation can be monitored in experimental animals using electronystagmography (Waespe et al., supra). Decreases in cycle (ie. increased rate) following administration of pharmacological agents would provide means for detecting lead compounds that may be therapeutic for mood disorders. In this respect, the test specimen is preferably a monkey, and PAN is preferably induced by cerebellar uvula and modulus destruction as for example described by Weaspe et al. (supra).

The invention also extends to a process for identifying a candidate therapeutic agent for alleviating a mood disorder, including the steps of measuring first perceptual rivalry rate in a test specimen, administering or applying a test compound to the test specimen, measuring second perceptual rivalry rate in the test specimen, and identifying a candidate therapeutic agent if said second perceptual rivalry rate is faster than said first perceptual rivalry rate. Preferably, said perceptual rivalry is binocular rivalry. Suitably, the test specimen is a human or animal.

In the case of the test specimen comprising an animal, the animal is suitably a cat, and in this regard, the rate of binocular rivalry is preferably determined by measurement of optokinetic nystagmus as for example described by Fries et al (1997, *Proc. Natl. Acad. Sci. USA* 94:12699–12704) which is incorporated herein by reference. Alternatively, the animal may be a monkey and in such a case, the binocular rivalry rate is measured by optokinetic nystagmus or by the method of Sheinberg and Logothetis (1997, supra).

7. Use of Diagnostic Method to Treat Unipolar Patients

The invention further provides a method of treating a patient with unipolar disorder, said method comprising the steps of determining an interhemispheric switch rate of the patient, comparing said interhemispheric switch rate with a range of reference interhemispheric switch rates associated with bipolar disorder, and administering to said patient a pharmacologically-effective dosage of a mood-stabilising drug when said interhemispheric switch rate is in said range. Preferably, the mood stabilising drug is lithium. Preferably, the interhemispheric switch rate is determined by perceptual alternation more preferably binocular rivalry. In the latter case, the drag is administered to the patient when the alternation rate is below 0.25 Hz, more preferably below 0.20 Hz, and most preferably below 0.15 Hz.

The inventors have found that there appears to be two unipolar disorder groups: ie. one group has normal alternation rates and the other group has slower than normal alternation rates but generally not as slow as bipolar subjects. These two groups may reflect different underlying biological abnormalities and therefore switch rates may be used to subtype unipolar disorder, preferably unipolar depression.

EXAMPLES

Example 1

Apparatus for Measuring Rate of Binocular Rivalry

Figure 2:
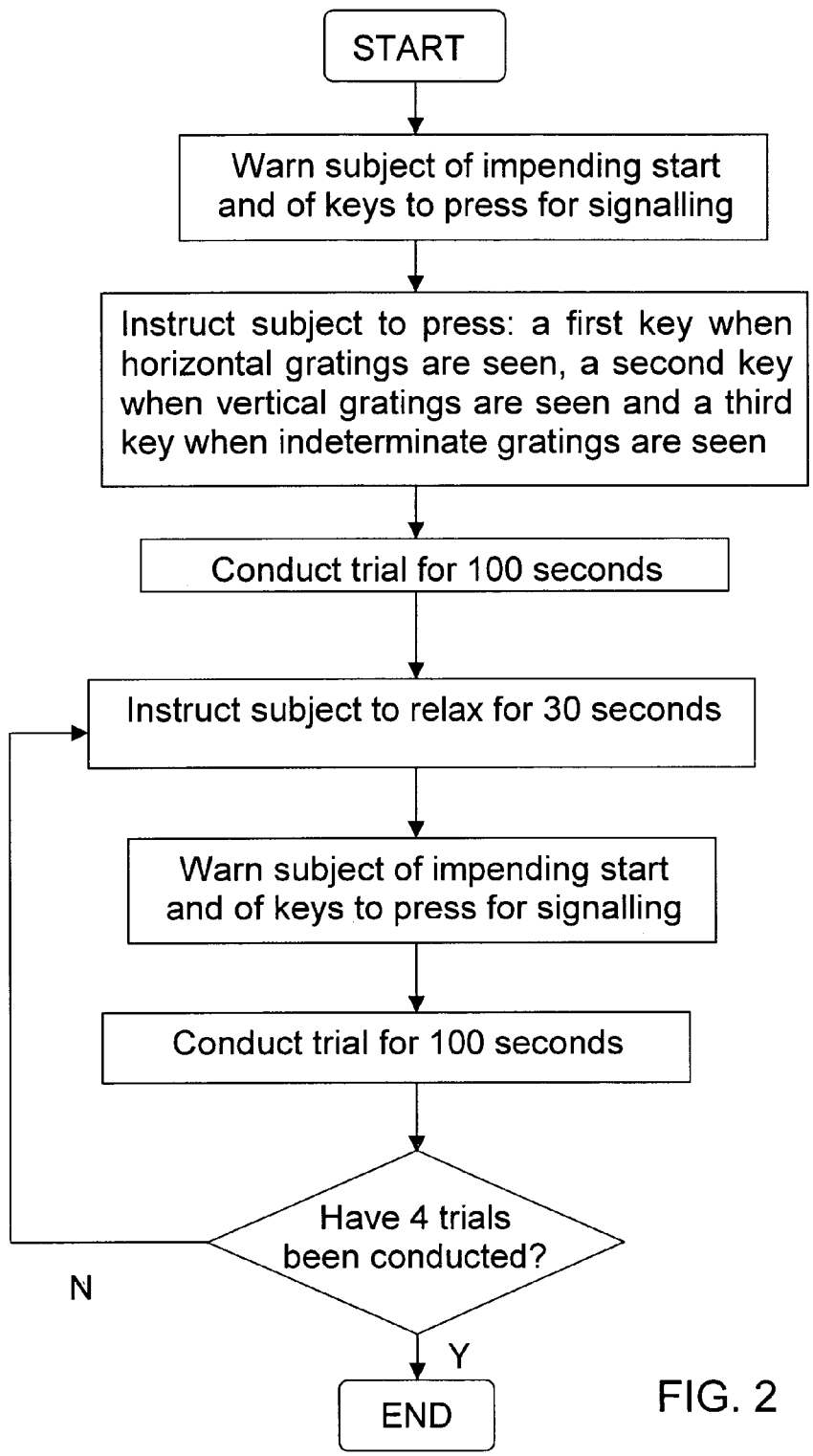
FIG. 2 shows a flow chart for a block or module of testing to determine a subject's binocular rivalry rate.

In one embodiment shown in FIG. 1, binocular rivalry is used as an indicator of mood disorder or predisposition therefor. Binocular rivalry is tested with a subject 1 seated three metres from a computer monitor 2 and wearing liquid crystal shutter goggles 3 to enable the presentation of vertical moving lines 4 to the left eye and horizontal moving lines 5 to the right eye. The stimuli subtend 1.5 degrees of visual angle with a spatial frequency of 8 cycles/degree moving at 4 cycles/second. The subject 1 presses one of three response buttons 6 to indicate their perceptual state (horizontal, vertical or mixed/indeterminate percepts). Rivalry testing is conducted over half an hour. There are three blocks of testing, each containing four 100 second trials interspersed with 30 second rests. Each block is interspersed with a two-minute rest. A non-limiting example of a block of testing is given in FIG. 2.

Alternation rate per second is calculated in a processing means such as a personal computer 7 by dividing the number of perceptual switches by the total time of rivalry, excluding mixed/indeterminate percepts. Other calculated indicators include a measure of image bias (total time spent viewing vertical lines divided by the total time spent viewing horizontal lines), autocorrelation (a measure of the independence of successive interval durations) and fit to the gamma distribution (a known feature of binocular rivalry). The latter two indicators may be used to verify reliability of subjects' subjective reports, as they are well known features of rivalry that are difficult to fabricate.

The inventors have found that binocular rivalry using orthogonal moving lines is particularly simple to implement and consistent in result. However, the use of other images has been reported in literature relating to binocular rivalry and the inventors are aware that other image combinations would be suitable and could be employed in the invention as for example described herein. Indeed, other devices for measuring interhemispheric switch rate can be used, such as monitors of the nasal cycle as described herein.

Example 2

Linkage Studies

The inventors' discovery of slow rivalry alternation rate in individuals with bipolar disorder, and in particular, relatives of individuals with such disorder, is potentially a major breakthrough in understanding the genetics of the disorder. There is no doubt that bipolar disorder is strongly heritable (Mitchell et al, 1993, *Aust. & New Zeal. J. Psych*. 27:560).

The identification of a trait-dependent marker for bipolar disorder will assist genetic linkage studies, and may lead to the identification of the underlying molecular defect. Gershon and Goldin (1986, *Acta Psych Scand* 74:113) proposed four basic criteria for markers to be considered risk factors for disease:

i. The biological variable should be associated with the disease at the population level and should clearly separate patients from controls, ii. Family and twin studies should conform that the variable is heritable;

iii. It should be a trait rather than a state marker, present in both the acute phase and in remission from the illness; and iv. It should be abnormal in relatives, including some asymptomatic relatives who would otherwise be considered to be carriers.

The data presented herein suggest that slow rivalry alternation rate in bipolar disorder may satisfy the first of these criteria. The heritability of the phenomenon in bipolar families will be examined by comparison of rivalry alternation rates in non-affected relatives and controls. Any demonstration of abnormal rates or bimodality would suggest the possibility that this would represent an alternative phenotypic marker for this illness.

Bipolar Families

Large bipolar pedigrees will be sought. Respective family members will be interviewed with the Diagnostic Instrument for Genetic Studies (DIGS; Nurnberger et al 1994, *Arch. Gen. Psych*. 51:849) and will have blood taken for genotyping.

Inheritance

The inheritance of rivalry alternation rates in the bipolar pedigrees will be examined. The major aim of this experiment is to determine whether rivalry alternation rates in the non-affected blood relatives of the bipolar families (i.e. those without bipolar or unipolar illness) differ from the rates found in control subjects. First, rivalry alternation rates in affected individuals, non-affected relatives and controls will be compared. Second, evidence of bimodality of rates in unaffected relatives will be examined.

Figure 6:
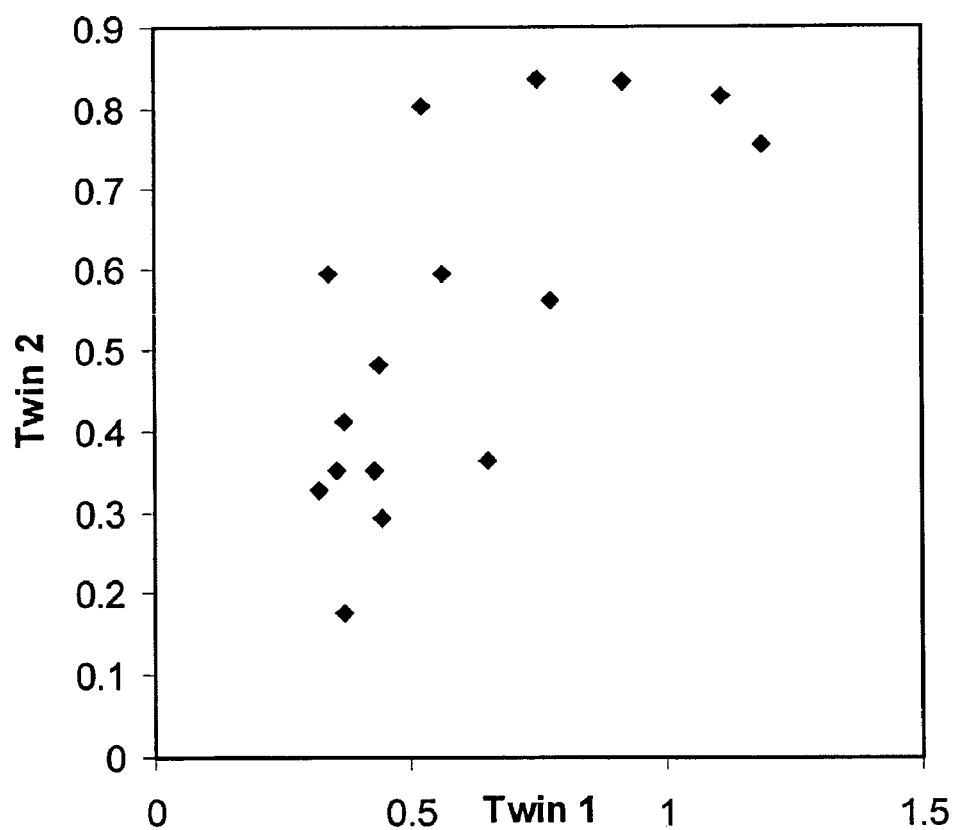
FIG. 6 shows the correlation of binocular rivalry rates in 16 pairs of monozygotic twins. The high correlation of switch rates (r=0.72) suggests that there is indeed a genetic contribution to binocular rivalry switch rate. Twins were tested with moving horizontal and vertical gratings using the same apparatus for testing and recording as in FIG. 1.
Figure 7:
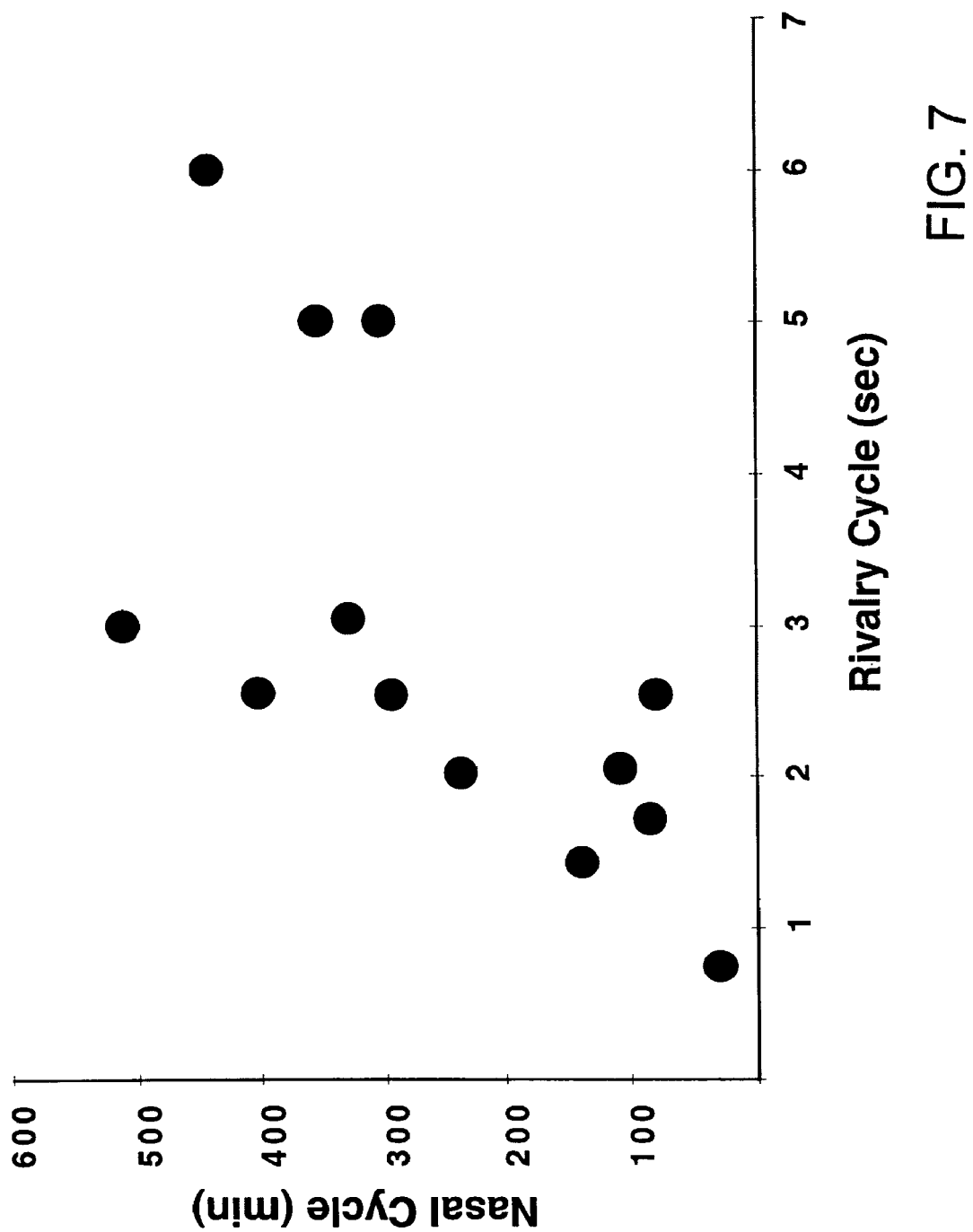
FIG. 7 shows a graph of nasal cycle length versus binocular rivalry cycle length. Individuals with slow nasal cycle also have slow binocular rivalry cycle and vice versa. The correlation of nasal cycle length to rivalry cycle length is grater than 0.6. This suggests coupling of interhemispheric oscillators similar to the coupling seen in circadian and ultradian oscillators in *Drosophila*. Determination of the nasal cycle length was by subjective report of nasal patency but can be objectively observed using nasal thermistors (Werntz et al., 1983), which is incorporated by reference herein.

While slower switch rates in affected individuals would be expected from studies described herein, slow switch rates in non-affected relatives would be confirmatory evidence of an alternative expression of the genetic trait for bipolar disorder. Twin pairs will also be examined to assess inheritance of rivalry alternation rate. Any demonstration of concordance of rivalry alternation rates in such pairs would be confirmatory evidence that this represented an alternative phenotypic expression of the bipolar genotype. A preliminary analysis of 16 pairs of monozygotic twins (FIG. 6) shows that there is a high correlation of switch rates ($r=0.72$) and this suggests that there is indeed a genetic contribution to binocular rivalry switch rate.

Example 3

Identifying a Candidate Therapeutic Agent for Alleviating or Preventing Mood Disorders (I)

Binocular Rivalry in Monkeys Detected by Their Behavioural Response.

*Macaca mulatta* monkeys are trained, while wearing liquid crystal shutter goggles, to fixate on a light spot on a computer monitor. They are then taught to pull and hold one of two levers if vertical moving lines are presented to both eyes, and to pull and hold a different lever if horizontal moving lines are presented to both eyes. In addition, they are trained not to respond to the presentation of different blends of horizontal and vertical moving lines. The stimuli subtend 1.5 degrees of visual angle with a spatial frequency of 8 cycles/degree moving at 4 cycles/second. Rewards of juice are provided for successful identification of visual stimuli during periods of random presentation of horizontal moving lines, vertical moving lines, or blended horizontal and vertical moving lines. When animals can accurately identify the different visual stimuli, binocular rivalry is induced using the liquid crystal shutters to present vertical moving lines to the left eye, and horizontal moving lines to the right eye. Eye position is monitored, and excursion significantly outside 3 degrees of visual angle aborts the observation period. Observation periods of up to 60 s are used. Alternation rate per second is calculated by dividing the number of perceptual switches by the total time of rivalry. Other calculated indicators include a measure of image bias (total time spent viewing vertical lines divided by the total time spent viewing horizontal lines), autocorrelation (a measure of the independence of successive interval durations) and fit to the gamma distribution (a known feature of binocular rivalry). Repeated observations are made over several days to determine the mean and standard deviation of the alternation rate. Putative compounds for the treatment or prevention of manic or depressive episodes may be given to monkeys acutely (eg. intravenously or orally) or chronically, over weeks. Effects of these compounds on accuracy in identifying vertical, horizontal and blended moving lines will be determined as a control. Rivalry alternation rate during exposure to test compounds will be determined, and compared to the alternation rate before, and after exposure to the test compounds. Dose response curves will be constructed. During chronic exposure to test compounds, the time course of the onset and recovery of effects on alternation rate will be determined. To obtain reliable test results, a lest should be conducted twice and the results averaged if comparable. A third test should be carried out if results are different, and the results from each test subsequently averaged.

Example 4

Identifying a Candidate Therapeutic Agent for Alleviating or Preventing Mood Disorders (II)

Binocular Rivalry in Monkeys Detected by Optokinetic Nystagmus.

*Macaca mulatta* monkeys are trained, while wearing liquid crystal shutter goggles, to attend to various visual stimuli (presented on a computer monitor) which subtend 1.5 degrees of visual angle. While anaesthetised with ketamine and xylazine, silver/silver chloride electrodes are implanted subcutaneously lateral to each eye, and above and below one eye to record horizontal and vertical movements respectively. These electrodes are then used to detect Optokinetic nystagmus (OKN) in the awake-trained monkeys. Optokinetic nystagmus correlates well with the perception of direction of motion of moving vertical lines. The accuracy of this assumption is tested in each animal by randomly presenting visual stimuli with vertical lines moving either left to right, or right to left. The stimuli subtend 1.5 degrees of visual angle with a spatial frequency of 8 cycles/degree moving at 4 cycles/second. Binocular rivalry is then established using liquid crystal shutters, and alternation rate calculated from the OKN. Pharmacological studies are conducted as described in Example 3.

Example 5

Identifying a Candidate Therapeutic Agent for Alleviating or Preventing Mood Disorders (III)

Periodic Alternating Nystagmus

A *Macaca mulatta* monkey is anaesthetised, and its cerebellum exposed by opening the dura and pia mater. A complete nodulo-uvulectomy is performed by suction ablation. This ablation includes removal of the lateral 2 mm of the modulus located rostrally. Silver/silver chloride electrodes are implanted subcutaneously lateral to each eye, and above and below one eye to record horizontal and vertical movements respectively. These electrodes are subsequently used to detect periodic alternating nystagmus. Postoperatively animals receive analgesics and antibiotics, and receive prophylactic promethazine HCl to prevent vomiting. Postural instability resolves over weeks. Periodic alternating nystagmus develops in the majority of awake animals so prepared minutes after they are placed in the dark. The rate of alternation is determined by recordings from the implanted electrodes. Pharmacological studies are conducted on the rate of alternation as described in Example 3.

Example 6

Identifying a Candidate Therapeutic Agent for Alleviating or Preventing Mood Disorders (IV)

Brainstem Slice Preparation.

Brains are removed from deeply anaesthetised rats or mice, and 200–400 micron transverse or horizontal slices are cut from the brain stem using a vibratome. Single slices are placed in a chamber and continuously perfused with physiological saline (ACSF, 32° C.). Bilateral recordings are made from single neurones using either low impedence extracellular electrodes, or intracellular glass electrodes. Low impedence electrodes may also be used to make bilateral recordings of field potentials reflecting the discharge of populations of neurones. Bilateral, simultaneous recordings are sought from neurones that exhibit spontaneous bistability. Such recordings are sought in paired nuclei including the locus coeruleus, pedunculopontine nucleus, periaqueductal gray nuclei, and the serotonergic raphe nuclei and any of multiple other brainstem or subcortical nuclei. Pharmacological studies are performed on bistable paired recordings by superfusing test compounds at appropriate concentrations. The reversible effects of compounds on the rate of discharge of bistable neurones is determined. Dose response curves are calculated. Intracellular recordings are used to determine the effects of test compounds on membrane properties of single neurones. To obtain reliable test results, a test should be conducted twice and the results averaged if comparable. A third test should be carried out if results are different, and the results from each test subsequently averaged.

Example 7

Identifying a Candidate Therapeutic Agent for Alleviating or Preventing Mood Disorders (V)

In Vivo Single Unit Studies

In vivo experiments are performed on rats or mice anaesthetised with pentobarbitone sodium (intraperitoneal), or ketone and xylazine (intramuscular). Anaesthesia is maintained respectively by bolus intravenous injections of pentobarbitone, or intramuscular ketamine. A heating pad is used to maintain body temperature at 36–37 degrees, as monitored by a rectal probe. Animals are placed in a stereotaxic apparatus, and a craniotomy performed to permit access to brain stem structures. Sites of recording is determined by sterotaxic coordinates, and where appropriate, by recording field potentials elicited by stimulating antidromically. At the end of each experimental session, recording sites are marked by use of electrolytic lesions, and identified histologically. Bilateral recordings are obtained from paired brainstem nuclei, including the locus coeruleus, pedunculopontine nucleus, periaqueductal gray nuclei, and the serotonergic raphe nuclei and any of multiple other brainstem or subcortical nuclei. Extracellular microelectrodes are used to record either single units, or field potentials. Bilateral, simultaneous recordings exhibiting spontaneous bistability are sought from single neurones or from populations of neurones from paired nuclei. Pharmacological studies are performed by administering test compounds intravenously. The reversible effects of compounds on the rate and characteristics of paired bistable recordings are determined.

EXPERIMENTAL

A Sticky Interhemispheric Switch in Bipolar Disorder

The present invention was stimulated by work that emphasises the contrasting cognitive styles of the cerebral hemispheres (Ramachandran, 1994, *Int. Rev. Neurobio.* 37:291–333). Stoke patients with anosognosia (denial of disease) usually have right-sided parietal lesions (McGlynn & Schacter, 1989, *J. Clin. Exp. Neuropsych.*, 11:143–205). Patients with similar left-sided lesions rarely exhibit anosognosia and are usually fully aware of their deficits. Ramachandran (1994, supra) therefore suggested that the left hemisphere's cognitive style is goal-directed with a coherent plan of action that denies or smooths over discrepancies, while the right hemisphere's style is that of a "devil's advocate" that monitors and seeks to raise discrepancies. If the lesioned hemisphere permits the opposite hemisphere to engage its preferred cognitive style unopposed, this would explain the observed hemispheric asymmetries associated with anosognosia.

Antithetical viewpoints of each hemisphere would pose problems for a neural executive that tried to act upon them simultaneously. From our observations of a fish with an interhemispheric switch that is apparent to visual inspection of its eye movements (Wallman et al. 1995, "Hemispheric Switching of Eye Movements in Sandlances". Abstract in *Nervous Systems and Behaviour: Proc. of the IV Int. Congress of Neuroethology*, Thieme Medical Publishers, New York), we hypothesised that in humans the complementary viewpoints of the hemispheres are adopted successively. In this way we could explain the mood shifts seen in bipolar disorder in terms of the cognitive style associated with the activated hemisphere: left hemisphere activation being associated with confidence, elation, or mania, according to the intensity and/or duration of activation, while an increasing degree of right hemisphere activation would be associated with caution, apprehension or depression.

Binocular Rivalry

To study the putative interhemispheric switch in bipolar subjects we have used binocular rivalry:—ie. the alternating perceptual states that arise when viewing different images, presented separately to each eye, in the same retinal location. We have suggested that competition for awareness during rivalry occurs between rather than within hemispheres (Miller et al. 1997, *Proc. Aust. Physio. Pharm. Soc.*, September, 68P; Pettigrew et al 1998, "A Hemispheric Switch in Binocular Rivalry?" *Proc. Aust Neurosci. Soc.* Abstract). Rivalry has been thought to be mediated by reciprocal inhibition of neurones in the separate channels for each eye, in early visual cortex (Blake, 1989, *Psychological Review*, 96:145). Recent single-unit (Sheinberg & Logothetis, 1997, supra) and psychophysical (Logothetis et al. 1996 supra; Kovacs et al. 1996, supra; Andrews & Purves, 1997, supra) studies however, support the notion that rivalry is a high level attentional process that cannot be explained by neural activity early in the visual pathway.

Since it has been suggested that in both normal and split brain subjects, the cerebral hemispheres can function independently of each other during perceptual and attentional tasks (Luck et al. 1989, *Nature* 342:543–545, Zaidel, 1995, "Interhemispheric Transfer in the Split Brain: Long term Status Following Complete Cerebral Commissurotomy" In Davidson and Hugdahl (eds) *Brain Asymmetry*, MIT Press, London, 491–532), we hypothesised that, the resolution of the conflicting visual information in binocular rivalry might be resolved by independent hemispheric function. Thus alternating visual awareness during rivalry would correlate with alternating hemispheric activation. To test this hypothesis we assessed the effect of, two unilateral hemisphere stimulating techniques, caloric vestibular stimulation and transcranial magnetic, stimulation (Miller et al. 1997, supra; Pettigrew et al. 1998, supra). The changes in rivalry characteristics that occurred following such hemispheric stimulation can be understood if rivalry is a between-hemisphere competition phenomenon. Within-hemisphere competition at any level would not predict an effect from unilateral hemisphere stimulation.

Methods

Normal subjects aged 19–55 (22 females and 27 males) were drawn from university students and employees. Subjects were screened by a medical practitioner for symptoms of mood disorder. Bipolar patients, aged 27–74 (9 females and 9 males), were recruited with the help of local psychiatrists and hospitals. They underwent an OPCRIT diagnostic classification (McGuffin et al 1991, *Arch. Gen. Psych.* 48:764–770) or had already been extensively evaluated for prior research purposes using a structured clinical interview for DSM-IIIR. Inclusion criteria were at least one admission for mania or an OPCRIT diagnosis of either bipolar disorder or bipolar disorder with psychotic features. All bipolar subjects were euthymic at the time of testing. The remaining bipolar patients were on one or a combination of the following medications: lithium, clonazepam, valproate, carbamazepine, a variety of antidepressants, haloperidol and risperidone. There was no significant difference between the rates of unmedicated subjects (n=3), the rates of subjects on lithium only (n), and the rates, of subjects on combination therapy (n=9). Accordingly, we have pooled the data for all bipolar subjects. Subjects were paid for their participation and gave written informed consent as part of a protocol approved by the University of Queensland Medical Research Ethics Committee.

In the case of corresponding studies concerning unipolar subjects, criteria for inclusion of these subjects were history for antidepressant medication and no previous history of manic episodes.

The aforementioned method is given only by way of example and in this regard, alternative means for diagnosing unipolar disorder, bipolar disorder or predispositions respectively therefor are also contemplated. For example, such diagnosis may be effected by measuring the number or fraction of particular perceptual intervals of unusually long duration relative to the mean perceptual interval duration.

Results

Figure 3:
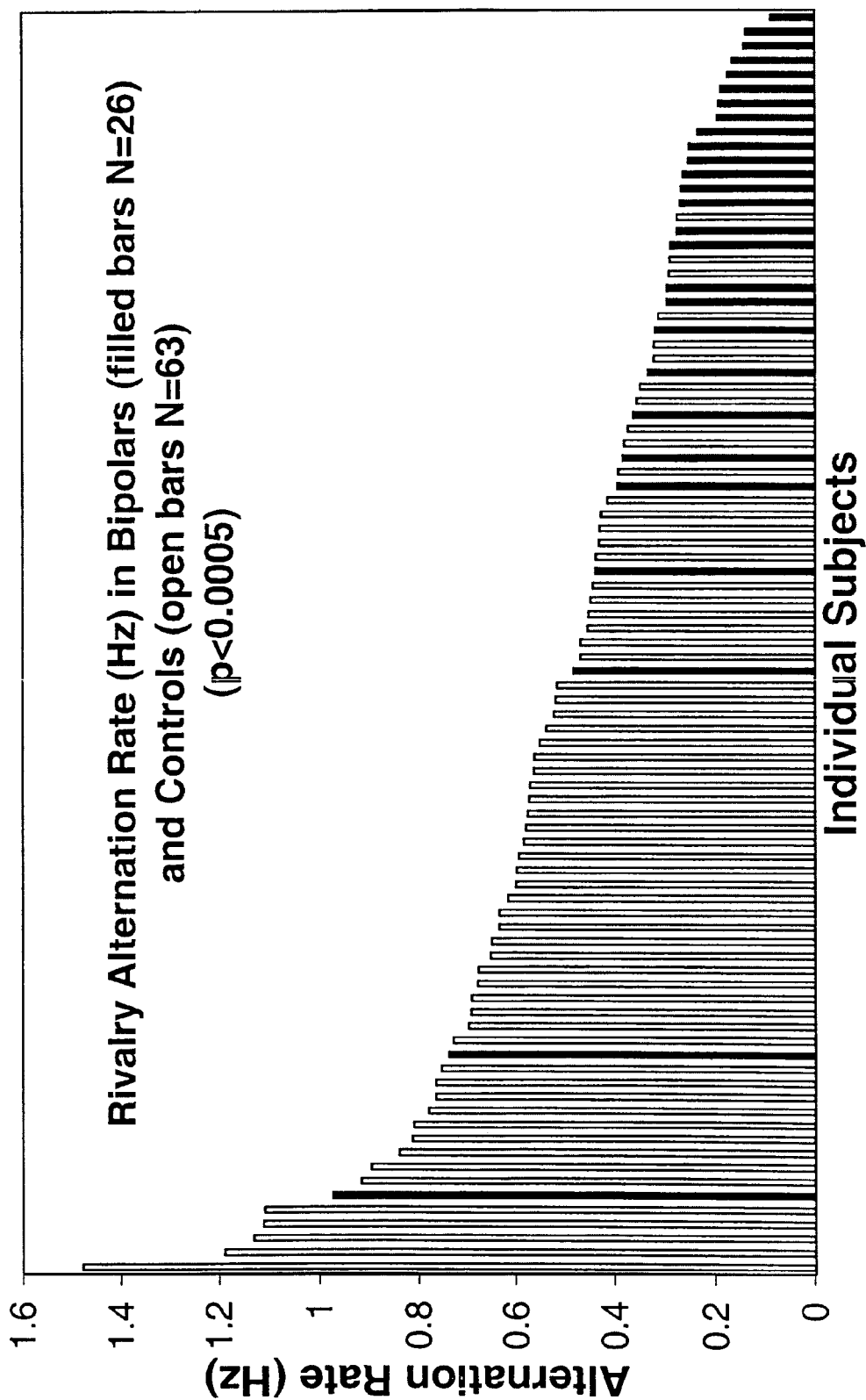
FIG. 3 shows the distribution of rivalry switch rate in normal and bipolar subjects. Distribution of rivalry switch rate in normal and bipolar subjects. The height of each column gives the mean rivalry switch rate for one individual over two blocks of trials totalling 20 min. Only a few individuals have short intervals, with a distinct plateau of common rates around 0.6 Hz and a long tail reaching out to slow rates. Bipolar subjects (n=26, median=0.26 Hz) have slow rates and are highly significantly different from normals (n=63, median=0.57 Hz, p<0.0001).

Bipolar subjects were clustered on the tail of the distribution representing slower alternation rate. This is shown in FIG. 3 which gives the distribution of alternation rates in bipolar (median=0.27 Hz) and non-clinical (median=0.60 Hz) subjects. These results are highly significant (Mann-Whitney U-test, Z=4.569, p<0.0005) and indicate that a rivalry alternation rate of less than 0.40 Hz is indicative of bipolar disorder or predisposition therefor. However, as with most clinical tests, there is a possibility of false positives or false negatives.

Figure 4:
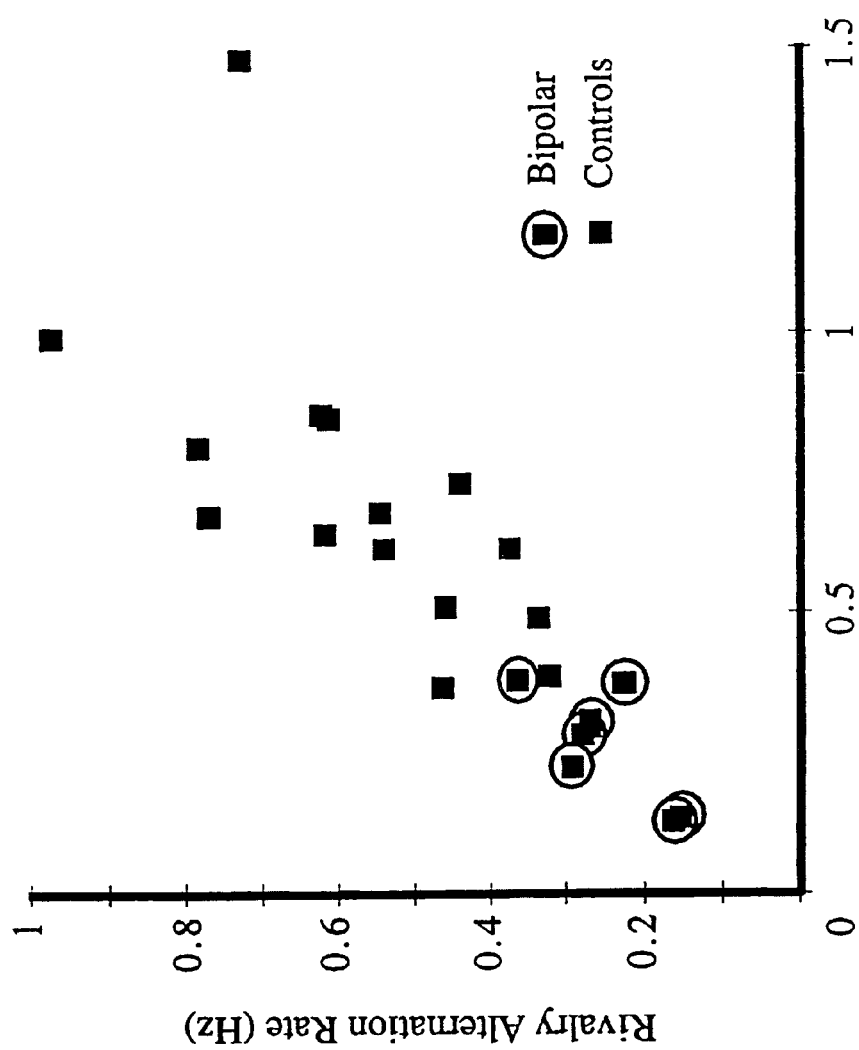
FIG. 4 shows test-retest correlation of rivalry alternation rate in bipolar and control subjects. Test-Retest Correlation of Rivalry Alternation Rate in bipolar and control subjects. There is a high correlation ($r^2$=0.83) between the rates obtained from the same individual on different occasions, indicating that this is a stable trait that would lend itself to genetic analysis.
Figure 5:
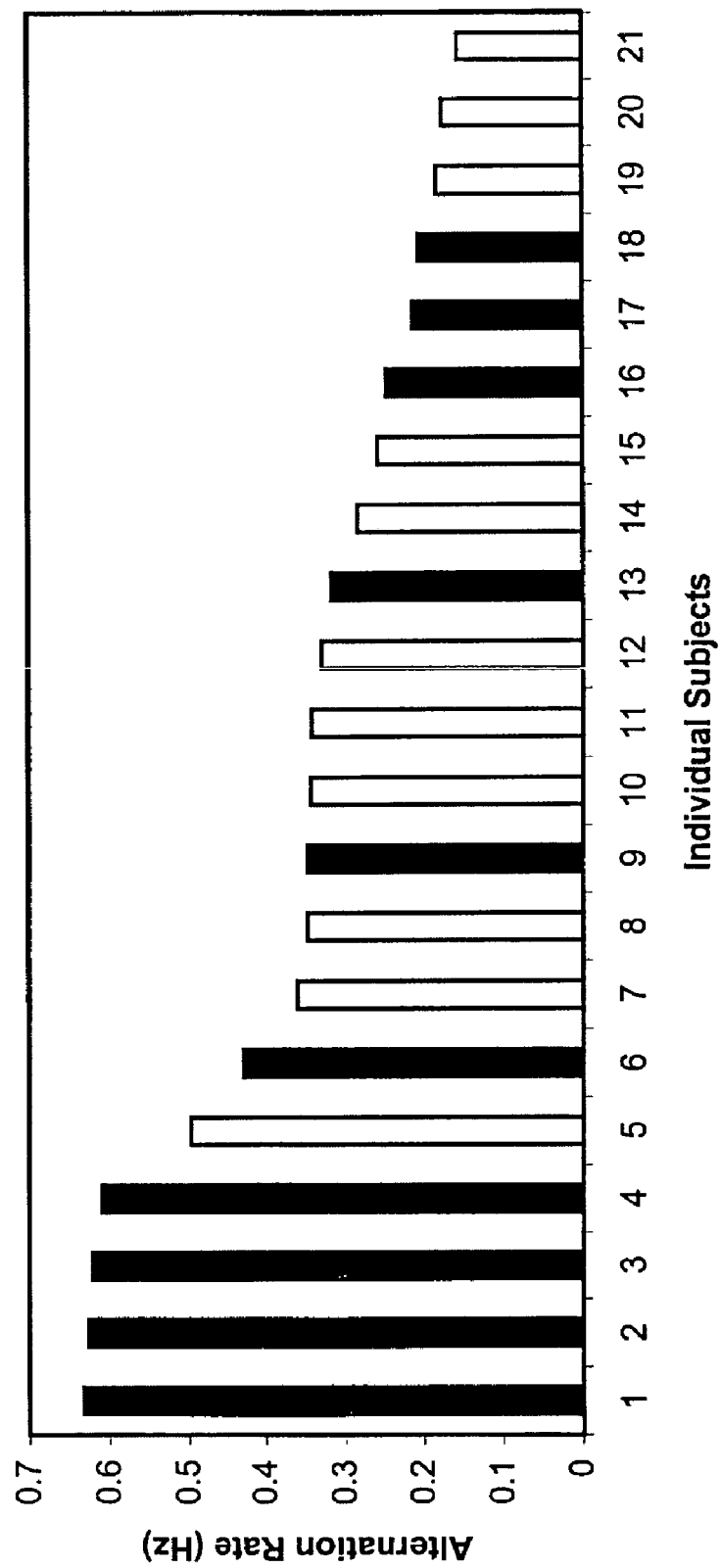
FIG. 5 shows the rivalry rates of bipolar subjects (open bars) and first degree relatives of bipolar subjects (black bars) tested with stationary vertical and horizontal gratings. The distribution is bimodal with approximately half the first degree relatives having rates faster than the bipolar subjects and the remainder, with rates as slow as bipolar subjects. Those slow switching relatives are likely to have inherited the genotype that predisposes to developing bipolar disorder while the faster switching relatives have not inherited this susceptibility.

The time intervals collected from a single subject undergoing rivalry form a gamma distribution (Logothetis et al 1996, supra). While different subjects all have gamma-like distributions, the scale of the abscissa varies considerably between subjects. The distribution of rivalry intervals across our population of subjects is also gamma-like with only a small number of individuals having intervals that are shorter than the mode of the distribution, compared with the extended tail of the distribution where individuals have long intervals. A given individual has a fairly repeatable distribution of intervals when retested. Although the bias for one of the two alternative rivalry states may vary from trial to trial, the overall rate is relatively constant. When subjects were retested several weeks or months later the test-retest correlation coefficient was around 0.80 (see FIG. 4).

Subjects with unipolar disorder (N=9) exhibit a slower than usual rivalry rate though to a lesser extent than bipolar subjects. In this regard, unipolar disorder may be diagnosed, or a predisposition therefor suggested, when the rate of perceptual alternation in the subject is in the range of between 0.35H and 0.45 Hz (Mann-Whitney U-test, Z=2.642, P=0.008).

Discussion

Genetics

We have suggested elsewhere (Miller et al 1997, supra) that an interhemispheric switching mechanism in binocular rivalry may be mediated by bistable oscillators (Marder et al 1996, *Physiological Reviews* 76:687–717) located in the brainstem. While the switch is likely to have top-down influences, the fundamental rhythm may be determined intrinsically, in the same way as for other bistable oscillators, by the number of cationic currents that drive the rate of depolarisation following the hyperpolarisation phase, with the rate proportional to the number of cationic currents present (Rowat & Selverston, 1997, *J. Comp. Neurosi.* 4:103–107; Marder, 1998, *Annu. Rev. Neurosci.* 21:25–45). If the slowed rivalry rate that we have observed in bipolar patients proves to be a reliable trait marker for the disorder, we would predict that the relevant genes would be associated with the many cationic currents that have been described so far. There are multiple different cationic channels, each of which might contribute to the rhythm of the switch. This functional multiplicity could explain the well recognised failure of linkage studies to settle on a single chromosomal locus (Adams et al 1998, *Am. J. Hum. Genet.* 62:1084–1091; McGue & Bouchard, 1998, *Annun. Rev. Neurosci.* 21:1–24). A quantitative trait such as slow rivalry rate may be more revealing in genetic studies than the more limited, qualitative information available from the presence or absence of clinical episodes.

A Model of Bipolar Disorder

Slow switches are "sticky" switches, because the intrinsic cationic currents driving the slower oscillator are reduced, making the switch more likely to be held down in one state by external synaptic inputs (Rowat & Selverston, 1997, supra). At first sight, the suggestion that the primary defect is a reduction in cationic channels, which would have a general effect of decreased neuronal sensitivity, conflicts with evidence of increased neuronal sensitivity in the form of elevated levels of G proteins (Mitchell et al 1997, *Am. J. Psych.* 154:218–223) and increased responsiveness of cAMP processes (Andreopoulos et at 1997, *Neuroscience Abstracts* 23:1676) in bipolar subjects. These apparent contradictions can be resolved if the primary effect of the decreased cationic channels on the timing of the oscillator is distinguished from the "downstream" effects on other parts of the brain, such as the cerebral hemispheres, where compensatory mechanisms may be employed to restore normal levels of excitability in the face of reduced cationic channel function. In other words, the hemispheres may be concerned more with neuronal excitability than with clock rate. Since many effective medications for bipolar disorder (eg. lithium) are known to decrease excitability via G-protein and cAMP mediated processes, we suggest that the mechanism of action may be upon these downstream effects rather than on the defect in the oscillator per se.

Since the cerebral hemispheres provide an important contralateral "top-down" synaptic input to the brainstem switch, a compensatory increase in sensitivity would lead to increased hemispheric output (in response to a stressor) and might therefore increase the likelihood that the switch will be held down ("stuck") on the side favouring that hemisphere. We therefore envisage a manic or depressive episode being the result of a stressor that causes the switch to be "stuck" in one of two positions:#unrelieved left hemisphere activation being associated with mania, in line with that hemisphere's cognitive style; unrelieved right hemisphere activation being associated with depression, in line with its style.

In view of the above, compounds which directly increase switch rate rather than acting on downstream effects of reduced cationic channels would represent a new mechanism of action for mood stabilisation. In this regard, reference may be made to a wide variety of possible modulatory agents of bistable oscillators described in Harris-Warrick (1991, *Annu. Rev. Neurosci.* 14:39–57) which is hereby incorporated by reference.

Hemispheric Asymmetries of Mood and Mood Disorder

Hemispheric asymmetries of mood and mood disorder have been widely discussed (Kinsbourne (ed), 1988, "*Cerebral Hemisphere Function in Depression*" American Psychiatric Press, Inc. Washington; Davidson & Hugdahl (eds), 1995, "*Brain Assymetry*" MIT Press, London, Ch. 13, 361–387). Imaging studies suggest that there is greater relative right prefrontal activation in depression#ie. left prefrontal 'hypometabolism'—which was not present whet subjects were re-scanned following clinical remission (Bench and Dolan 1995, *Psych. Med*. 25:247–251; Martinot et al 1990, *Am. J. Psych*. 147:1313–1317). EEG studies also support greater right activation in depression (Henriques & Davidson, 1991, *J. Abn. Psych*. 100:535–545). Activation asymmetries favouring the left hemisphere have been reported in mania (Migliorelli et al 1993, *J. Neuropsychia. Clin. Neurosci*. 5:379–383). In keeping with these activation asymmetries, it has been shown that TMS of prefrontal cortex is therapeutic for depression when administered on the left (George et al. 1994, *Am. J. Psych*. 154:1752–1756; Pascual-Leone et al 1996, *The Lancet* 348:233–237).

Unilateral hemisphere inactivation using sodium amobarbitol has also been associated with asymmetric mood sequelae. Inactivation of the left hemisphere has been shown to more commonly induce negative moods on subjective measures (Christianson et al 1993, *Brain and Cognition* 23:127–144) while objective measures of affect showed crying to be related to left hemisphere injections and laughter/elation to right-sided injections (Lee et al 1990, *Brain and Cognition* 12:267–280). Lesion studies (Robinson & Downhill, 1995, "Lateralization of Psychopathology in Response to Focal Brain Injury" In Davidson and Hugdahl, supra, Ch. 23, 693–711) have been particularly illuminating with respect to asymmetries. Robinson and Downhill (1995, supra) report that left-sided lesions in prefrontal and basal ganglia regions are more commonly associated with depression than similar lesions on the right; and secondary mania more commonly follows right-sided lesions (basotemporal cortex, orbitofrontal cortex, basal ganglia, thalamus) than similar left-sided lesions.

Robinson and Downhill (1995, supra) suggest that lesion asymmetries may be the result of asymmetric pathophysiologic responses to injury. While such mechanisms may be relevant, studies of emotion and mood in normal subjects (Davidson, 1995, supra; Heller & Nitschke, 1997, *Cognition and Emotion* 11:637–661) support the notion of underlying physiological asymmetries which would also explain the lesion data. This interpretation does not exclude asymmetric response to injury since asymmetries of physiologic function may be reflected in neurochemical asymmetries and subsequent pathologic response asymmetries.

Slowed Oscillator for Frontal and Limbic Regions

The notion of alternating hemispheric activation has been suggested before and is supported by electrophysiological and psychological studies of ultradian rhythms (<20 hrs duration) of cerebral dominance (for a review see Shannahoff-Khalsa, 1993, supra). The typical period for such rhythms is in the minutes to hours range. The oscillator for binocular rivalry targets regions at high stages of visual processing in temporo-parietal cortex, based on neurophysiological evidence from monkeys undergoing rivalry (Sheinberg & Logothetis, 1997, supra). An interhemispheric switch for cognitive style and mood, would be likely to engage frontal and limbic regions and to have a period similar to that of reported ultradian rhythms of cerebral dominance (ie. minutes to hours). A slowing of the oscillator for rivalry, from 1–2 seconds to 10–20 seconds, would not account for any of the clinical phenomenology of bipolar disorder. The slowing of an oscillator for temporo-parietal cortex might also be accompanied by a proportionate slowing of the putative oscillators that govern interhemispheric switching in other regions. There is a precedent for such coupling in *Drosophila* where a single mutation may simultaneously reduce the rate of both fast (ultradian) and slow (circadian) oscillators (Hall & Rosbash, 1988, *Annu. Rev. Neurosci*. 11:373–393). The question of coupled oscillators is clearly relevant to variants of bipolar disorder such as seasonal affective disorder (Teicher et al 1997, *Arch. Gen. Psych*. 54:124–130; Madden et al 1996, *Arch. Gen. Psych*. 53:47–55; Corbera, 1995, *Bio. Rhythm Res*. 26:253–260).

Conclusion

In the present specification, there is presented a readily testable neurophysiological model of bipolar disorder. It is based on our studies of interhemispheric switching and binocular rivalry, as well as a substantial body of evidence on hemispheric asymmetries of mood and mood disorders. Our model also incorporates the possible molecular defects of different cationic channels whose multiplicity may help explain the difficulties encountered in genetic linkage studies. Identification of the molecular defects may in future lead to novel therapeutic approaches.

Interhemispheric Switching Mediates Perceptual Rivalry

Binocular rivalry refers to the alternating perceptual states that occur when different images, such as orthogonal contours, are presented simultaneously, one to each eye. For each image, periods of perceptual dominance alternate with periods of perceptual suppression, usually every few seconds. Until recently, this phenomenon was thought to result from reciprocal inhibition between monocular neurones (ie. neurones responsive to input from one eye only) in separate channels in primary visual cortex (V1) (Blake R, 1989, *Psychological Review*, 96:145–167). This model of binocular rivalry is inconsistent with the findings of Leopold and Logothetis (Leopold and Logothetis, 1996, *Nature*, 379: 549–553) who demonstrate that only a small percentage of neurones in V1 exhibit activity that correlates with a monkey's perceptual reports during rivalry. Moreover, of those neurones in V1 whose activity was correlated with the monkey's reports, all but one were binocular (ie. responsive to input from either eye). Sheinberg and Logothetis (1997, *Proc Natl Acad Sci USA*, 94:3408–3413) then showed that high in the visual pathway in inferotemporal cortex and the superior temporal sulcus, around 90% of neurones demonstrate activity that is dependent on the perception of an effective visual stimulus.

Psychophysical studies are also inconsistent with the low-level or eye competitor models of binocular rivalry which postulate that rivalry occurs at a stage prior to binocular convergence. Our group has replicated and quantified the convincing demonstration by Diaz-Caneja in 1928 (Diaz-Caneja E, 1928, *Annales D'Oculistique*, 721–731) that eye-competition cannot alone explain the psychophysics of binocular rivalry. These and related experiments (Kovacs at al, 1996, *Proc Natl Acad Sci USA*, 93:15508–15511) show that the brain is able to organise aspects of each eye's presented image into two rivalling coherent images. Such perceptual periods in which there is re-organisation of components of each eye's image into coherent rivalling patterns, cannot be accounted for by eye-competition models of rivalry.

In accordance with the compelling Diaz-Caneja (1928, supra) evidence firm psychophysical and single-unit studies, that binocular rivalry is a high level phenomenon between stimulus representations (or organised coherent representations), two recent NM studies of humans undergoing binocular rivalry demonstrate brain activation in regions of the visual processing hierarchy beyond V1 (Lumer et al., 1998, *Science*, 280:1930–1934; Tong et al, 1998, *Neuron*, 21:753–759). Despite this evidence, there are no models of the neural mechanisms that mediate this high-level competitive process. Here we present a readily testable model, the interhemispheric switch hypothesis, which suggests that each cerebral hemisphere adopts one of the rivalling representations and that competition for awareness occurs between, rather than within, each hemisphere.

Neuropsychological studies with normal and split-brain subjects support the notions of hemispheric independence and dynamic modularity (Zaidel E. Clarke J M, Suyenobu B: *Hemispheric independence: a paradigm case for cognitive neuroscience.* In *Neurobiology of Higher Cognitive Function* 1990, eds. Scheibel A B, Wechsler A: The Guilford Press, New York, 297–355; Luck et al., 1989, *Nature*, 342:543–545). The contrasting cognitive styles of the hemispheres (Ramachandran V S, 1994, *Int Rev Neurobiol*, 37:291–333) further suggest that behavioural and perceptual conflict might be resolved by alternating hemispheric activation. Evidence for such hemispheric alternations in humans can be found in the literature on ultradian rhythms of cerebral dominance (Shannahoff-Kalsa D, 1993, *Int J Neurosci*, 70:285–298) but a periodicity in minutes-hours is suggested rather than the seconds-long periodicities seen in binocular rivalry. Birds demonstrate interhemispheric switching in song production (Suthers R A, 1997, *J Neuobiol*, 33:632–652) and brainstem mediated oculomotor alternations are evident in fish (Pettigrew et al., 1999, *Curr Biol*, 9:421–424) and humans (Baloh et al., 1976, *Brain*, 99:11–26).

To test the interhemispheric switch hypothesis of binocular rivalry, we first examined the effect of caloric vestibular stimulation on the perception of rivalling vertical and horizontal drifting gratings. PET (Bottini et al., 1994, *Exp Brain Res*, 99:164–169) and fMRI (Vitte et al., 1996, *Exp Brain Res*, 112:523–526) studies have shown that caloric stimulation causes activation in contralateral hemispheric structures that are involved in attentional processing (Posner and Petersen 1990, *Ann Rev Neurosci*, 13:25–42) and binocular rivalry (Lumer et al., supra) (e.g. temporo-parietal, insular and anterior cingulate cortex). In a clinical context, this technique can temporarily ameliorate left-sided neglect and anosognosia (denial of disease) associated with right hemisphere damage (Ramachandran V S, supra; Vallar et al., 1993, *Brain*, 116:71–86). The ability of caloric stimulation to activate contralateral structures implicated in attentional processing and binocular rivalry suggests that, if rivalry is a between-hemisphere competition phenomenon, caloric stimulation should alter the temporal properties of the competitive process. Specifically, the baseline perceptual predominance of one image relative to the other, should be altered by unilateral hemisphere activation of regions involved in binocular rivalry (see FIG. 11). Within-hemispheric competition at any level does not predict an effect from such unilateral hemisphere activation.

We next tested predictions that binocular rivalry occurs at the same level as other reversible figures, by assessing the effect of caloric stimulation during viewing of the Necker Cube. Similar effects of caloric stimulation on both binocular rivalry and Necker Cube alternations would be further support for the notion that these phenomena share a common neural mechanism (Logothetis N K, 1998, *Phil Trans R Soc Lond* B, 353:1801–1818; Walker P. 1975, *Perception and Psychophysics*, 18:467–473). A stimulation-induced change in the baseline predominance of either perceptual configuration of the Necker Cube would indicate that interhemispheric switching also mediates the alternations of these bistable perceptual phenomena in these experiments, we were also interested to see whether sham caloric stimulation with body temperature water would have any effect on perceptual alternations.

Figure 9B:
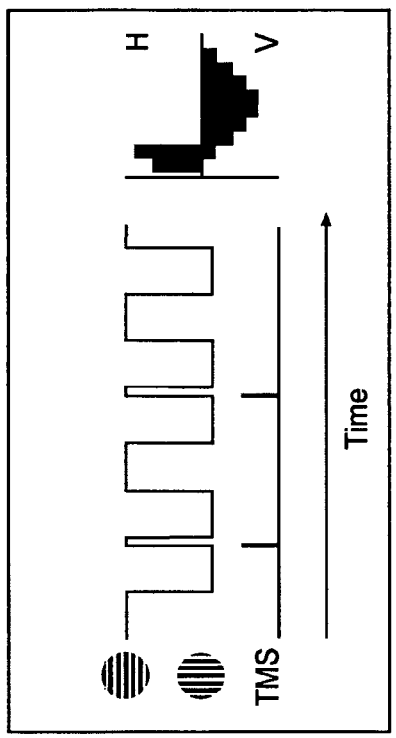
FIG. 9 shows a set-up for transcranial magnetic stimulation (TMS) and binocular rivalry experiments and the perceptual interference effects predicted by the interhemispheric switch hypothesis. (a) The circular coil delivers a single pulse to the temporo-parietal region of left hemisphere. The subject views orthogonal stationary gratings (see methods) and reports their perceptual alternations using two response keys, one of which triggers the magnetic stimulation. (b) The time course of perceptual alternations shows the predicted pattern of interference effects when the TMS is triggered by a switch to the horizontal percept. The interhemispheric switch hypothesis suggests that if the left hemisphere adopts the horizontal image, TMS applied to this hemisphere when the horizontal image is perceptually dominant will disrupt this representation and allow the vertical percept to assume dominance. The theoretical frequency histogram depicts very short horizontal interval durations. (c) When the stimulation is delivered to the same hemisphere but at the opposite phase of the perceptual switch (ie. triggered when the subject reports a switch to the vertical percept), disruption of the left hemisphere should have little effect since the vertical representation resides in the right hemisphere. Thus the theoretical frequency histogram for this contingency shows normal interval durations. Actual rather than theoretical frequency histograms for TMS's effect on rivalry alternations are shown in FIG. 13.
Figure 9C:
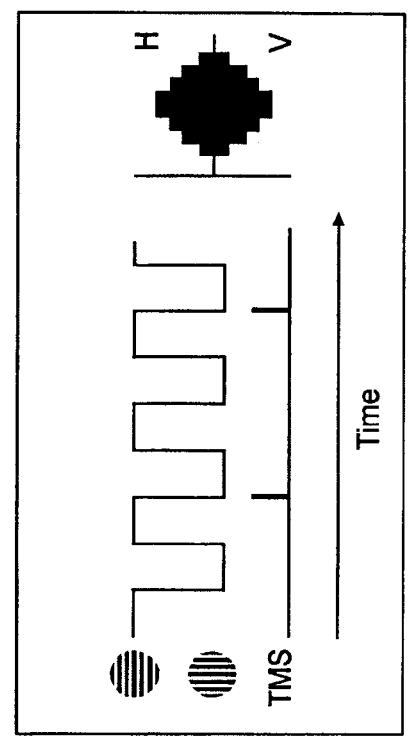
Figure 9A:
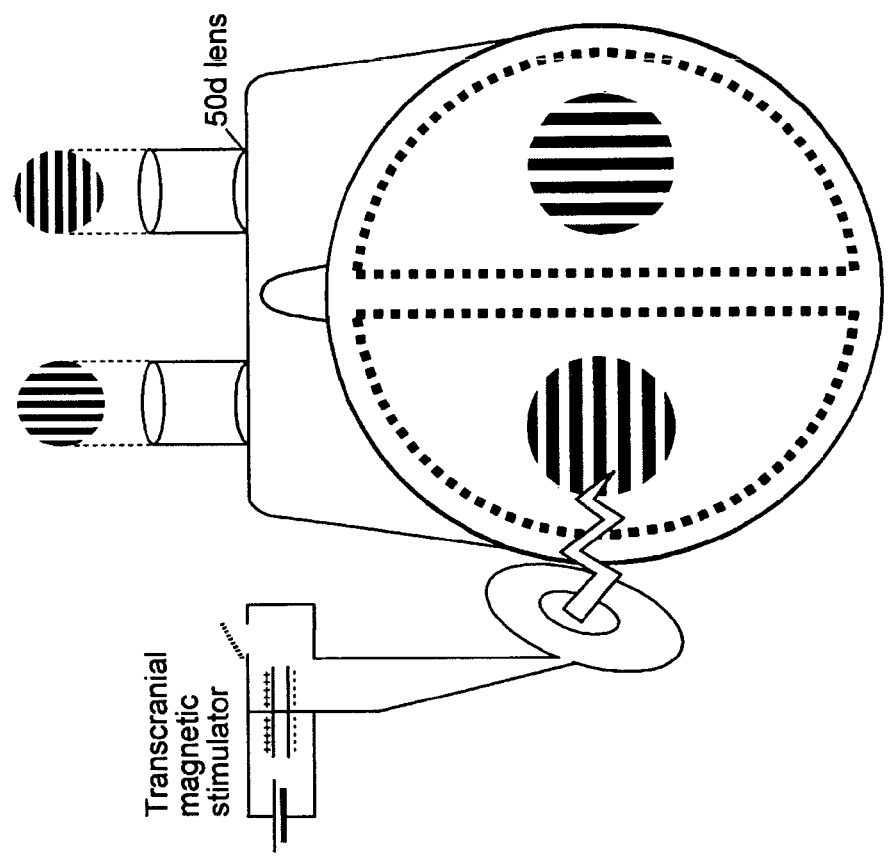

Finally, since the longer time course of caloric stimulation in relation to rivalry does not allow a direct assessment of the switching process itself we used unilateral single pulse transcranial magnetic stimulation (TMS), with its high temporal precision, to assess whether this would perturb the rivalry process in a manner that supports the interhemispheric switch hypothesis. The predictions for this experiment are: (i) unilateral hemisphere disruption due to TMS would disrupt that hemisphere's image representation and would thus cause perceptual disruption if the TMS is applied during perceptual dominance of that image; (ii) disruption of a hemisphere's image representation should have little effect on perceptual alternations if the TMS is applied when that image is perceptually suppressed. Thus a phase-specific pattern of interference effects is expected from unilateral hemisphere disruption with TMS if binocular rivalry is indeed, an interhemispheric switching phenomenon (see FIG. 9).

Results

Figure 10:
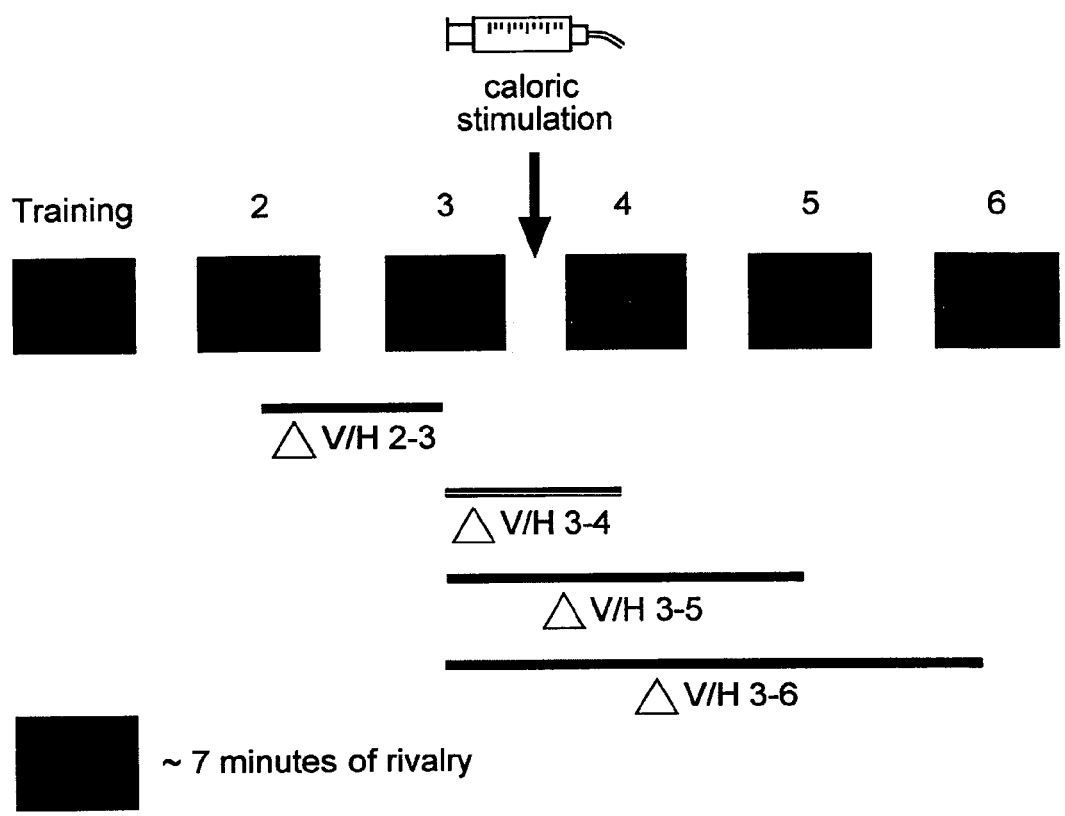
FIG. 10 shows an analysis procedure for caloric stimulation and binocular rivalry experiments. There are six blocks of rivalry each representing approximately seven minutes of viewing. Each block contains four 100-second trials separated by 30-second rest periods and each block is separated by a 2-minute rest period. The first block is considered training and discarded before analysis. Blocks 2 and 3 are pre-stimulation blocks, while 4, 5 and 6 are post-stimulation blocks. The predominance ratio is calculated by dividing the total time spent perceiving the vertical gratings by the total time spent perceiving the horizontal gratings, excluding mixed percepts. The resulting V/H ratio is log-transformed before analysis. Since there is random variation in this V/H ratio between two pre-stimulation blocks, to show an effect of caloric stimulation, there must be greater absolute magnitude of change in the V/H ratio between blocks 3 and 4 (random variation plus experimental effect) compared with the random change seen between blocks 2 and 3. Comparison of the V/H 2–3 change with the V/H 3–5 change (and the V/H 3–6 change) allows an indication of the stimulation's decay. The left hemisphere activation group (n=18) demonstrated a greater V/H change following stimulation compared with that seen prior to stimulation (p>0.05) and the effect was largely diminished by the fifth block (though not in all subjects). We were less able to demonstrate greater than baseline shifts in predominance for the right hemisphere activation group (n=14, p=0.72). Results were not significant for a control group of twelve subjects who underwent the entire protocol minus the caloric stimulation (p=0.21).
Figure 11A:
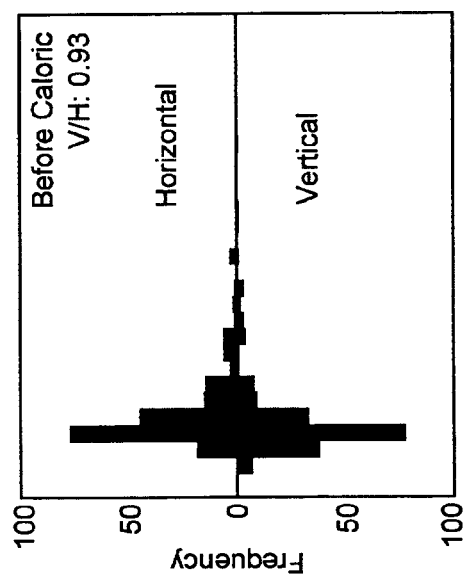
FIG. 11 shows the effects of caloric vestibular stimulation on two individuals' perceptual alternations in binocular rivalry. In both cases the predominance of one perceptual alternative is shifted by left hemisphere activation (right caloric stimulation). These changes are demonstrated in the frequency histograms of interval durations for each rivalling image. The shifts are also reflected by the predominance ratios shown in the top right hand corner of each of the histograms. In the first subject's case, (a) a baseline horizontal bias of V/H=0.93 was increased to (b) V/H=0.54 following caloric stimulation. This was the usual direction of change for left hemisphere activation. The second subject also illustrates a post-stimulation change, beginning with (c) a horizontal grating bias of V/H=0.94 which was reversed to (d) a vertical bias of V/H=1.26 following stimulation. The direction of shift for this subject is exceptional but suggests that designation of image to hemisphere may not always be fixed. This subject's results along with a number of other reasons (see text) also makes interpretations based on residual eye-movements, difficult to accept. The effect of caloric vestibular stimulation on the predominance of rivalling images supports the interhemispheric switch hypothesis and the data across all subjects (see text) suggests that the horizontal percept is usually adopted by the left hemisphere.
Figure 11B:
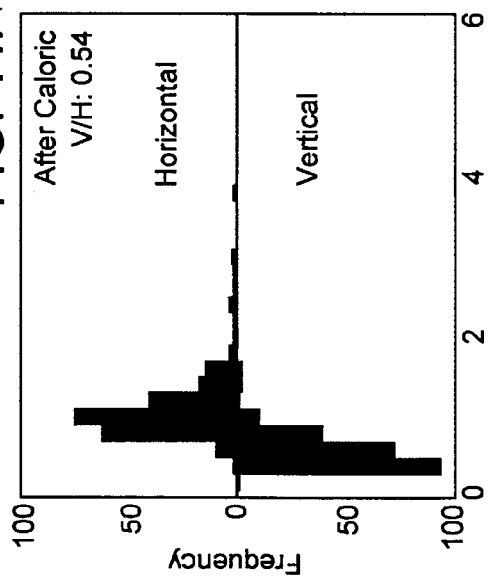
Figure 11C:
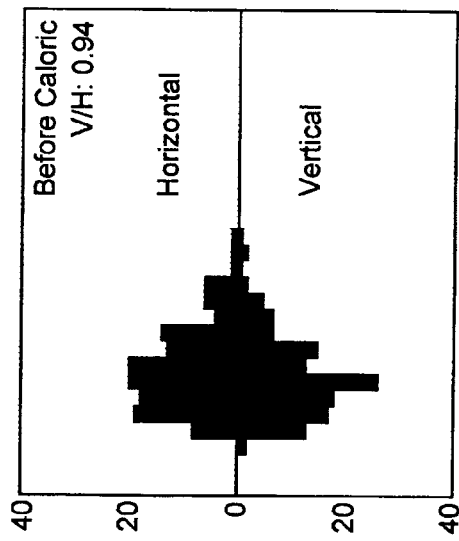
Figure 11D:
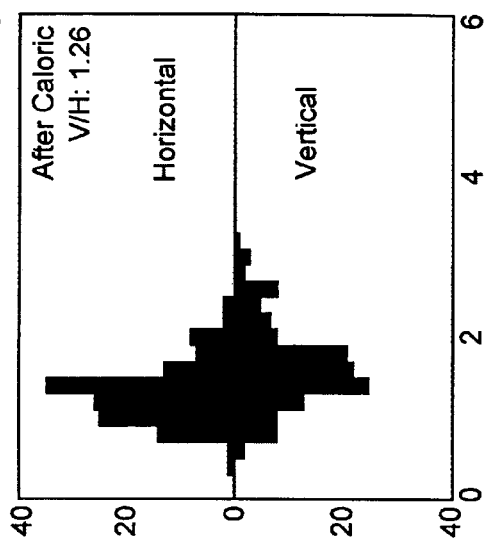

Results of caloric stimulation's effect on two subjects' rivalry alternations are presented in FIG. 11, where it can be seen from the frequency histograms that caloric stimulation produces a change in predominance (reflected by the V/H ratio, the ratio of total time spent perceiving the vertical and horizontal gratings, excluding mixed percepts). In individuals, the effect ranged from strong to absent. Our group analysis (see FIG. 10) compared the absolute magnitude of change in the V/H ratio between pre-stimulation block 2 and pre-stimulation block 3 (a measure of the normal fluctuation in V/H ratio) with the absolute magnitude of change between pre-stimulation block 3 and post-stimulation block 4 (a measure of the experimental effect plus normal variation). This comparison yielded statistical significance for the right caloric (left hemisphere) stimulation group (Wilcoxon signed-ranks test, $n=18$, $p<0.05$) and was not significant for a control group of twelve subjects who underwent the entire protocol minus the caloric stimulation ($p=0.21$). The delta V/H comparisons, in the left hemisphere stimulation group, between blocks 2–3 and 3–5 ($p=0.31$) and between blocks 2–3 and 3–6 ($p<0.72$) indicate that the effect of caloric stimulation was largely diminished by the fifth and sixth blocks of rivalry.

Further analysis demonstrated that left hemisphere activation consistently increases the predominance of the horizontal grating ($p<0.05$). This effect was due primarily to a reduction in mean vertical interval durations ($p<0.05$) while the mean horizontal interval duration did not change significantly ($p=0.59$). These temporal changes are reminiscent of Levelt's finding (Levelt W J M, 1966, *Br J Psychol*, 57:225–238) that increasing the stimulus strength of one presented image has little effect on its mean interval duration but decreases the mean interval duration of the other image. The same effect was observed in preliminary experiments in which the eye-f presentation was reversed suggesting that the left hemisphere bias for horizontal may be linked to the stimulus itself rather than the (contralateral) eye-of-presentation. It is possible that this bias is due to the link between a cultural bias for horizontal scripts and the known left hemisphere bias for language processing. Left caloric stimulation (right hemisphere activation), was less effective at producing shifts in predominance above baseline fluctuation ($n=14$, $p=0.72$). Alternation rate (z) increased following both right ($p<0.05$) and left ($p<0.05$) caloric stimulation.

Figure 12A:
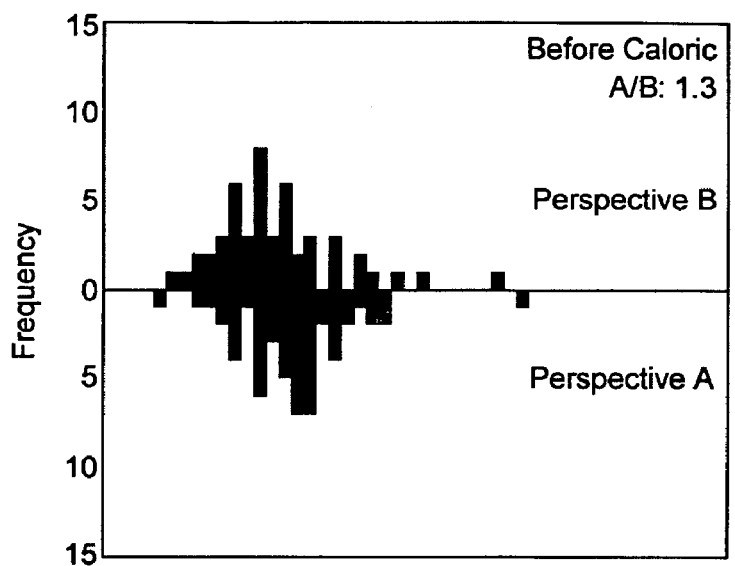
FIG. 12 shows the effect of caloric vestibular stimulation on perceptual alternations of a reversible figure, the Necker cube. Right caloric stimulation (left hemisphere activation) shifts a baseline perspective bias (A=lower square face closer to observer; B=upper square face closer to observer; ratio calculated as for binocular rivalry and excludes indeterminate percepts) of A/B=1.3 (a) to A/B=0.85 (b). Overall, subjects demonstrated shifts in both directions following stimulation, indicating that, unlike for binocular rivalry, designation of perceptual configuration to hemisphere is arbitrary. Also shown (c) are the raw data for a single subject demonstrating normal baseline perceptual alternations, with roughly equal time spent experiencing each perspective, and the effect of caloric stimulation which virtually eliminated the ability to perceive one perceptual alternative. The subject alternated between perspective A and the 'undecided' response option (where no depth was perceived) following left hemisphere activation. This dramatic effect may be related to the fact that this subject received prolonged iced water irrigation compared with other subjects. The effect of unilateral hemisphere activation on Necker cube alternations is further evidence that binocular rivalry and reversible figures share a common neural mechanism and suggests to us that this mechanism is interhemispheric switching.
Figure 12B:
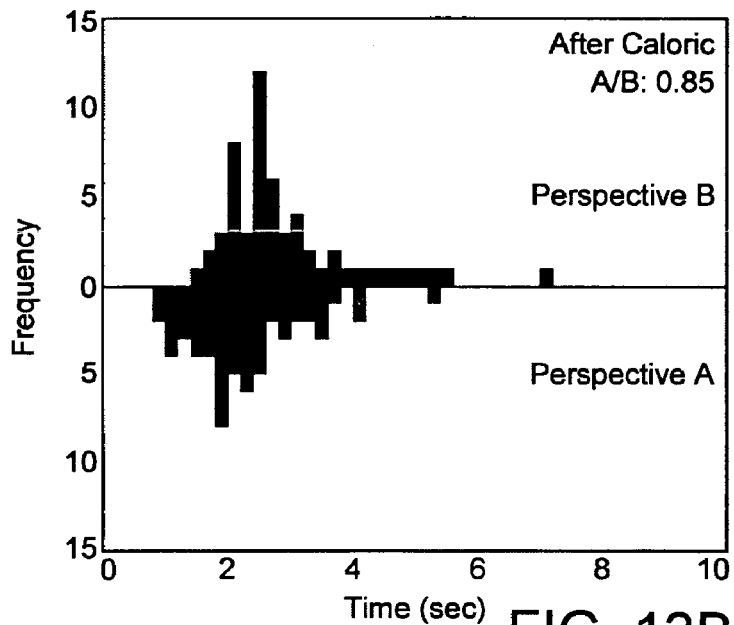
Figure 12C:
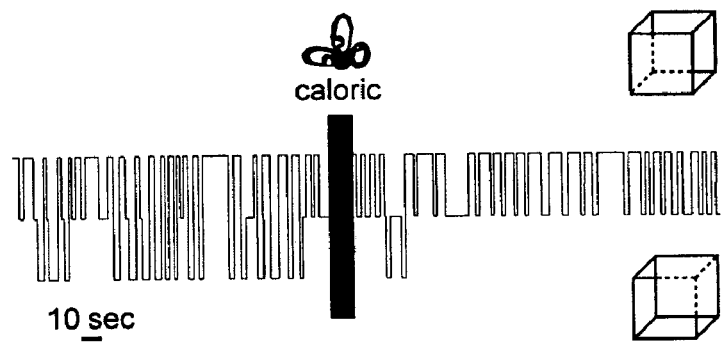

Since the effect of caloric stimulation on predominance was most striking for left hemisphere activation, we concentrated on this hemisphere for the Necker Cube experiments. The effect of right ear caloric stimulation on Necker cube alternations was dramatic in one subject (FIG. 12c) who had normal baseline perceptual alternations, but demonstrated an almost complete inability to see one perspective following caloric stimulation. His post-stimulation responses alternated between one clear perspective and the 'undecided'/indeterminate option where no depth was perceived. Other subjects showed a reversal of predominance following right ear caloric stimulation (FIG. 12a, 12b) similar to the effect seen with binocular rivalry. While the magnitude of the changes varied with the subject, perhaps according to the duration of the stimulation, left hemisphere activation caused a change in perspective predominance greater than baseline fluctuations (Wilcoxon signed-ranks test, n=10, p<0.05). This result did not occur for control (n=10, p=0.41) or sham stimulation (n=10, p=0.59) conditions. The caloric stimulation shifts in Necker cube perspective bias occurred in both directions, suggesting that designation of perspective to hemisphere is more arbitrary than for binocular rivalry where the data support a preferential association between the horizontal percept and the left hemisphere. Alternation rate of Necker cube reversals did not change significantly following caloric stimulation. The predominance results demonstrate that, as for binocular rivalry, unilateral (left) hemisphere activation by caloric stimulation affects the relative time spent perceiving the two Necker cube perspectives and thus supports interhemispheric switching as the neural mechanism of reversible figures.

Figure 13B:
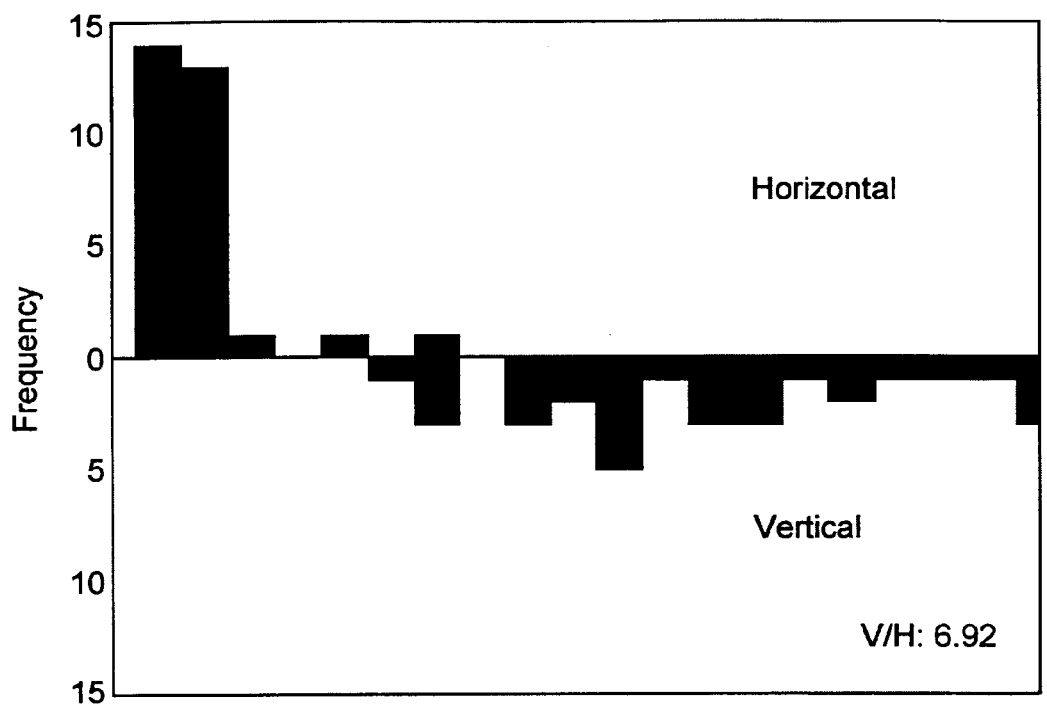
FIG. 13 shows the effect of left hemisphere transcranial magnetic stimulation on a single subject's binocular rivalry alternations. There is a marked interference with percepts when left hemisphere TMS is contingent on one direction of perceptual switch but not when the contingency is at the opposite phase. (a) If TMS was delivered when the subject signalled a switch from the vertical to the horizontal percept, there was an mediate reversion to the vertical percept, indicated by a dramatic shortening of the horizontal interval durations. The histogram only plots the vertical intervals just before stimulation and the horizontal intervals just after stimulation. (b) When TMS was administered at the opposite phase (when the subject signalled a switch from the horizontal to the vertical percept), it had minimal influence upon interval durations. This histogram only plots the vertical intervals just after stimulation and horizontal intervals just before stimulation. That one stimulation contingency but not the other affects rivalry alternations supports the interhemispheric switch hypothesis. Phase-specific interference effects such as those shown here are difficult to explain using a within-hemisphere competition model of binocular rivalry.
Figure 13A:
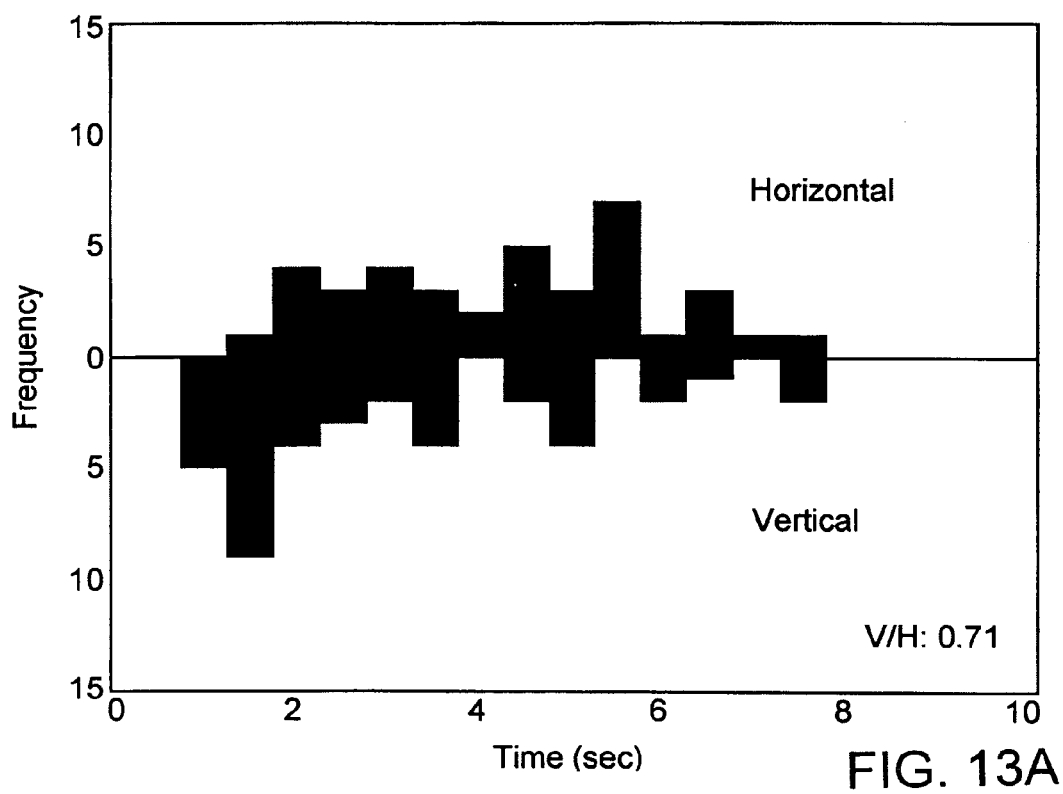
Figure 14:
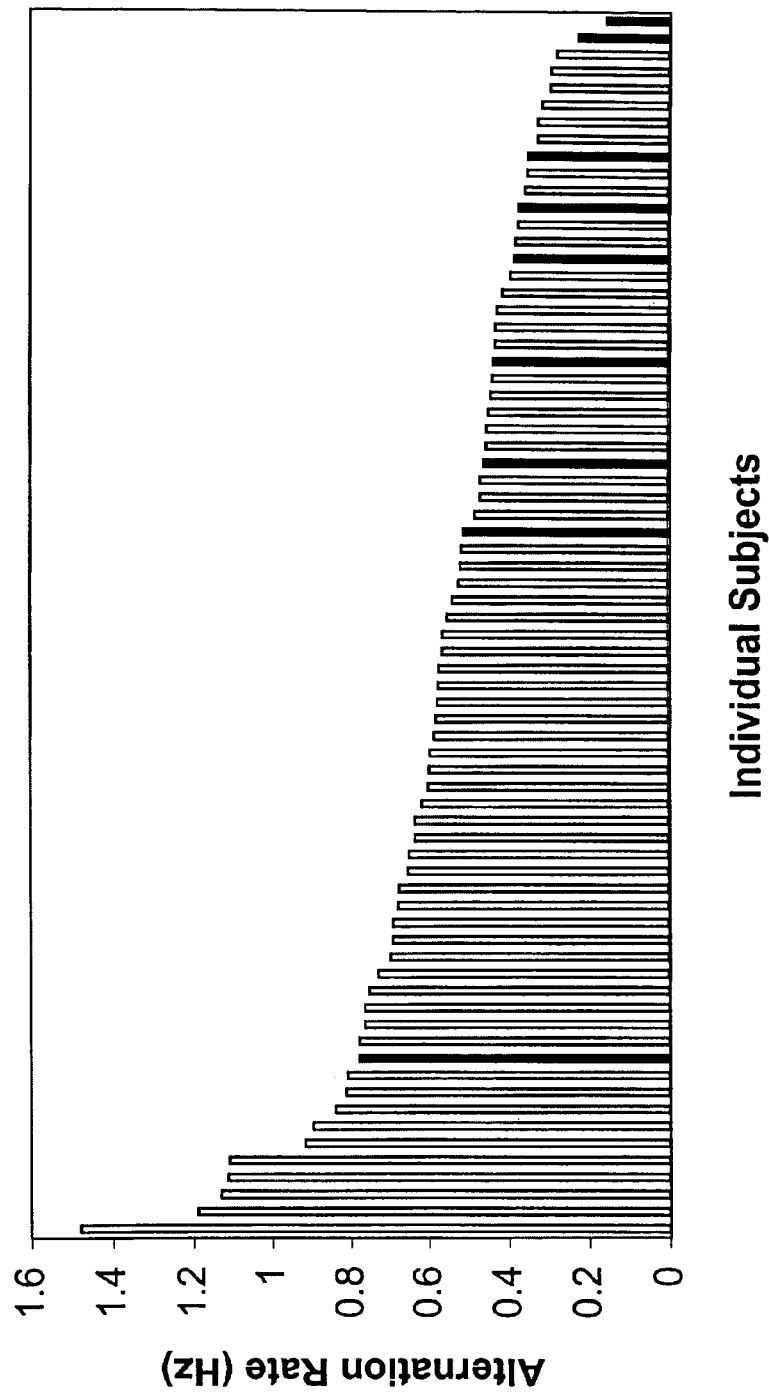
FIG. 14 shows the rivalry rates of non-clinical controls (open bars) and unipolar subjects (black bars) tested with moving vertical and horizontal gratings. There appears to be two groups: ie. one group has normal alternation rates and the other group has slower than normal alternation rates but generally not as slow as bipolar subjects.

FIG. 13 shows that application of a TMS pulse to one hemisphere (temporo-parietal region) had a disruptive effect on binocular rivalry which was, as predicted, phase-specific. In particular, left hemisphere stimulation, applied just as the percept was switching from vertical to horizontal, caused a reversion to vertical (brief or enduring, depending on the subject and stimulation intensity). There was minimal effect of the same stimulation when the TMS pulse was timed to occur at the opposite perceptual switch. Phase-specific interference effects occurred in five of the seven subjects tested. We attribute the variability between subjects to the difficulty of simultaneously establishing both a threshold stimulation intensity and an optimal location. These difficulties aside, the hypothesis of interhemispheric switching is supported by the striking positive findings that one stimulation contingency can alter the rivalry process while the opposite phase of stimulation has little effect even though delivered to the same hemisphere.

Discussion

Evidence for the Interhemispheric Switch Hypothesis of Perceptual Rivalry

Our results demonstrate that unilateral caloric vestibular stimulation particularly left hemisphere stimulation, influences the alternation patterns of binocular rivalry and reversible figures. We have also demonstrated a phase-specific effect of unilateral transcranial magnetic stimulation on rivalry alternations. The findings that unilateral hemisphere activation alters the predominance of perceptual states in binocular rivalry and reversible figures, and that unilateral hemisphere disruption has phase-specific interference effects in binocular rivalry, suggest to us that between-hemisphere competition is the neural correlate of these perceptual phenomena. We suggest that each hemisphere preferentially represents one image or perspective, and perceptual alternation reflects competition between the hemispheres for visual awareness. This view is in keeping with the suggestion that it is the stimulus representations rather than the eyes that rival during binocular rivalry.

The asymmetry we observed in caloric-induced interference effects should be interpreted with caution at this stage. The lack of a change in predominance above baseline fluctuations for the right hemisphere activation group may be explained by the following interpretation. A recent fMRI study of humans undergoing binocular rivalry found right-sided activation asymmetry during rivalry (Lumer et al., supra). This study did not separately analyse regional activation for each direction of perceptual switch and hence could not assess the interhemispheric switch hypothesis. Since activation patterns were assessed by combining both directions of perceptual switch in this study, the finding of asymmetric activation in right fronto-parietal regions suggests that these regions may be important in gating perceptual alternations and may be functionally quite distinct from the regions responsible for the image representations themselves. Reports that right-sided frontal lesions cause the perception of only one of the two possible perspectives of the Necker cube (Meenan and Miller, 1994: *Neuropsychologia*, 32:1145–1149) support this notion of a right-lateralised anterior gating region. Thus activation of the right hemisphere by left caloric stimulation might interfere with this gating process and may thus mitigate any expected shifts in predominance.

Hemifields and Hemispheres

In thinking about our model of interhemispheric switching, it is important not to be limited by spatially-symmetric notions of hemifield representations in V1. Although the patchwork contour rivalry used by Diaz-Caneja shows that rivalry does not occur between the cerebral hemispheres (Logothetis, 1998, supra) at a level in which the hemifields are represented separately, the single-unit data (Leopold and Logothetis, 1996, supra; Sheinberg and Logothetis, 1997, supra) and fMRI studies (Lumer et al., 1998, supra; Tong et al., 1998, supra) demonstrating high-level processing regions as the most likely site of rivalry, suggest that the hemispheres cannot be considered irrelevant a priori to the resolution of rivalling images. The binocular neurones in inferotemporal cortex whose activity correlates with monkeys' reported percepts, can process information presented to either hemifield as indicated by their properties of bilateral receptive fields and ipsilateral field loss following section of the posterior corpus callosum and anterior commissure (Gross et al., Inferior Temporal Cortex as a Pattern Recognition Device. In *Computational Learning and Cognition: Proceedings of the 3$^{rd}$ NEC Research Symposium* 1993, ed. Baum E, 44–73). Indeed, involvement of the hemispheres may help to explain the phenomenon of coherence. Diaz-Caneja's experiments [supra], our replication of these experiments and the chromatic patchwork experiments of Kovacs et al. (1996, *Proc Natl Acad Sci USA*, 93:15508–15511), all suggest that the brain is able to group or bind image segments that fit together irrespective of their eye-of-origin. The interhemispheric switch model suggests that the brain groups or binds the segments of each coherent image in separate hemispheres. This suggestion is compatible with the principles of image selection in rivalry elucidated by Logothetis (1998, supra) however our model has the selection process occurring independently, and in alternation, for each hemisphere.

Eye Movements

It is at least possible that the observed stimulation-induced predominance shifts actually result from residual nystagmic eye movements rather than the effect of contralateral cortical activation. We feel this is highly unlikely for a number of reasons. Firstly, the subject illustrated in FIG. 11b demonstrates that although most left hemisphere activation subjects have stimulation-induced shifts that decrease the mean vertical interval durations, not all subjects exhibit this pattern. Residual (horizontal) eye movements could not explain this shift towards a reduction in mean horizontal interval duration. Moreover, it has been shown that microsaccades do not alter the activity of neurones in inferotemporal cortex (Leopold and Logothetis, 1998, *Exp Brain Res*, 123: 341–345).

Results for the Necker Cube experiments also can't be explained by eye movements because the shift in configuration predominance occurred equally in both directions yet residual eye movements could only be occurring in one direction. The TMS results, which strongly support the interhemispheric switch hypothesis, may or may not involve eye movements. However since the TMS was delivered to the same hemisphere for both stimulation-contingencies, any effect due to eye movements should be seen in both stimulation-contingencies. This was clearly not the case as illustrated in FIG. 13.

It has been shown that patients with bipolar disorder (manic depression) who are treated with lithium have increased saccades during smooth pursuit tasks (Holzman et al., 1991, *Biological Psychiatry*, 29:1001–1015). If it is suggested that residual saccedes account for our observed stimulation-induced reduction in the mean vertical interval duration, one might assume that the increased saccadic activity during smooth pursuit in bipolar subjects would cause them to have faster than usual alternation rates due to reduction in mean interval durations of one or both images. We have shown exactly the opposite. Bipolar disorder is associated with slowed rivalry rates (a trait marker, independent of medication) and many of our bipolar subjects were on lithium treatment at the time of testing (Pettigrew and Miller, 1998, *Proc R Soc Lond* B, 265:2141–2148).

Brainstem Oscillator or Corpus Callosum?

The highly-developed corpus callosum connecting the human hemispheres may immediately suggest itself as a site for the proposed interhemispheric switch. We think that this is an unlikely site, and predict that split-brain subjects will nevertheless show perceptual alternations. We suggest that the primary mechanism of interhemispheric switching involves different subcortical bistable oscillator circuits related either to the short period perceptual alternations studied here or long-period alternating hemispheric activity (Pettigrew and Miller, 1998, supra; Shannahoff-Khalsa D, 1993, supra). The suggestion that a subcortical bistable oscillator mediates interhemispheric switching is based on both comparative considerations and clinical evidence in humans. Bistable oscillators are well-studied in invertebrates (Marder and Calabrese, 1996, *Physiological Reviews*, 76:687–717) and interhemispheric switching has been observed in the brains of birds (Suthers, 1997, supra) and fish (Pettigrew et al., 1999, supra) that lack a corpus callosum. Moreover, in human patients with midline cerebellar or brainstem damage, a roughly 90-second oscillator has been described that shows side-to-side alternation of eye movements (Baloh et al., 1976, supra). This oculomotor alternation, known as periodic alternating nystagmus, is believed to be a brain stem phenomenon and is accompanied by perceptual alternations during binocular rivalry consistent with our proposals concerning interhemispheric switching (Miller and Pettigrew, in preparation). The role of the brainstem in mediating synchronous neural activity (Munk et al., 1996, *Science*, 272:271–274) will be particularly interesting if temporal correlation (Engel et al., 1997, *Cerebral Cortex*, 7:571–582) of units with similar preferred stimuli is shown to be important at high levels of the visual pathway during binocular rivalry.

Conclusions

We have presented a readily testable neurophysiological model of perceptual rivalry based on the perceptual interference effects of unilateral hemisphere activation and disruption. Our results suggest that during perceptual rivalry, each hemisphere represents one of the competing images or perceptual configurations and perceptual alternations correspond to brainstem-mediated hemispheric alternations. The interhemispheric switching model also has clinical relevance because of the findings that patients with bipolar disorder have a slower switch rate for both binocular rivalry (Pettigrew and Miller, 1998, supra) and reversible figures (Hunt and Guilford, 1933, supra). Finally, in relation to neural mechanisms of conscious experience, the hypothesis of interhemispheric switching suggests that awareness of visual information during perceptual rivalry is not uniformly distributed in both hemispheres at the same time.

Materials and Methods

Binocular Rivalry

Figure 8B:
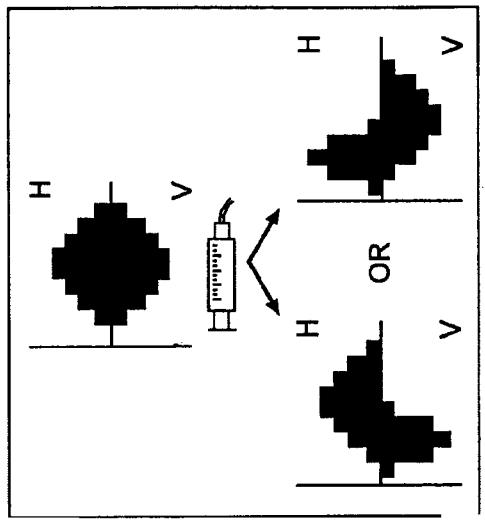
FIG. 8 shows a set-up for caloric stimulation and binocular rivalry experiments (a) and the perceptual interference effects predicted by the interhemispheric switch hypothesis (b, c). The rivalry set-up (a) shows a right-drifting vertical grating being presented to the left eye and an upward-drifting horizontal grating being presented to the right eye using liquid crystal shutters to restrict the presentation of each image to its intended eye. The orthogonal gratings induce binocular rivalry and the subject's report their perceptual alternations using response keys on a keyboard. The caloric stimulation procedure involves irrigating the external ear canal with iced water until subjects report vertigo and examiners observe nystagmus. The stimulation acts via the semicircular canals and brainstem and results in activation of contralateral structures (indicated in red) known to be involved in attentional processing and binocular rivalry (see text). The expected interference effects on rivalry alternations from such unilateral hemisphere activation (according to the interhemispheric switch hypothesis) are depicted in the theoretical frequency histograms shown in (b) and (c). These represent the frequency (y-axis) of horizontal and vertical perceptual intervals in seconds (x-axis) during the rivalry viewing period. In (b), there is no baseline predominance of either horizontal or vertical percepts so unilateral hemisphere activation might be expected to induce either a horizontal (bottom left) or vertical (bottom right) predominance. In (c), there is a baseline predominance of the horizontal percept that might be expected to disappear (bottom left) or even reverse to a vertical predominance (bottom right) following unilateral hemisphere activation by caloric stimulation. Actual rather than theoretical frequency histograms are shown in FIG. 8.
Figure 8C:
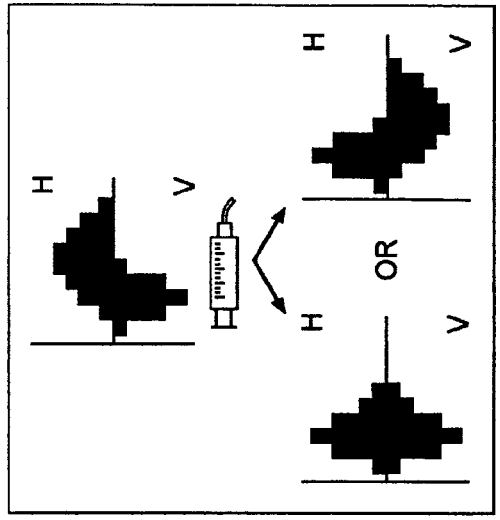
Figure 8A:
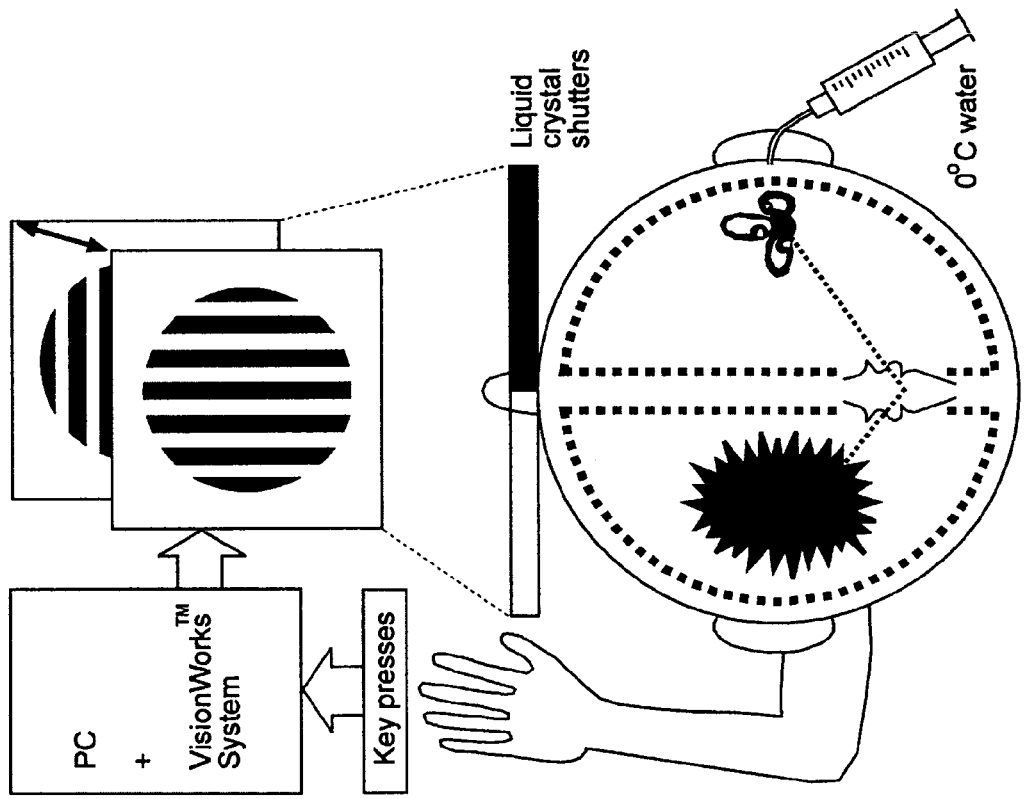

Thirty-two right-handed male and female subjects ranging from 18 to 54 years of age underwent cold caloric stimulation of either the right (n=18) or left (n=14) ear. Twelve control subjects underwent the full protocol minus the stimulation. Written, informed consent was obtained according to a protocol approved by the University of Queensland's Medical Research Ethics Committee. A Vision Works™ display with liquid crystal shutters was used to present an upward-drifting horizontal (square-wave) grating to the right eye while simultaneously presenting a right-drifting vertical grating to the left eye (see FIG. 8). This arrangement was reversed in some subjects to test whether biases were based on eye-of-origin or on the stimulus. The liquid crystal shutters allow the fields of view for each eye to be superimposed, with both horizontal and vertical targets occupying the same spatial location, so no training in fixation was required. The stimuli were presented in a circular patch and subtended 1.5 degrees of visual angle with spatial frequency of 8 c/deg moving at 4 c/sec. Contrast of the gratings was 0.9. Subjects sat three metres from the monochrome (green) computer monitor and recorded their perceptual alternations by pressing one of three keyboard response buttons for vertical, horizontal or mixed percepts. The latter were removed before analysis. Baseline perceptual alternations were recorded for half an hour. This was followed by caloric stimulation and a further half-hour of rivalry data collection. Each half-hour session was divided into three blocks, consisting of four 100 second trials. Each trial was separated by a 30-second rest period, and each block by a two-minute rest period. The first block was considered a training block and was discarded before analysis. The V/H ratio values (see text) were log transformed before statistical analysis.

Necker Cube

Ten right-handed males (and a further subject shown in FIG. 8*c*), aged 18–25, were tested on three occasions. The Necker cube was presented on a matt white surface 120 cm from the subject and at eye level. The cube subtended 7.20×8.0° (height×width) of visual angle and had a central fixation cross (0.5°×0.5°). Subjects were asked to maintain gaze on the fixation point and to record their perceptual alternations using a keyboard with a response key for each of the percepts and a third option for 'undecided' or indeterminate percepts or if their gaze strayed from the fixation point. The latter were remove before analysis. Alternations were recorded for half an hour, divided into three blocks each with three 100-second trials. Each trial was separated by a 60-second break and each block by a 4.5-minute break. Subjects then had (i) five minutes rest, (ii) sham stimulation-using water at body temperature, or (iii) cold caloric stimulation of the right car. A further half-hour of data was then collected. The A/B ratio values (see FIG. 12 legend) were log transformed before statistical analysis.

Caloric Stimulation

Cold water irrigation was administered by a medical practitioner using a 50 mL syringe and soft silastic tubing from a butterfly cannula. Head position was 30 degrees from horizontal bringing the lateral semicircular canal into the vertical plane. The tubing was inserted into the external auditory canal until it was adjacent to the tympanum. Iced water was then instilled until the subject reported vertigo and the examiner observed nystagmus (usually following 1030 mL of iced water irrigation). Subjects demonstrated nystagmus with the brisk phase in the direction contralateral to the ear stimulated. Post-stimulation data collection began when all signs of nystagmus and subjective vertigo had ceased.

Transcranial Magnetic Stimulation

Single pulse TMS was applied to the left temporo-parietal cortex using a 90 mm circular coil (Magstim 200™, The Magstim Company). Magnetic stimuli were triggered when the subject signalled a perceptual switch either to the vertical percept in one trial or to the horizontal percept in the other. The intensity of stimulation was varied between 0.66 and 1.1 T according to the subject. The rivalry apparatus used in these experiments consisted of two 1 cm (diameter) by 2 cm translucent plastic tubes each with a 50 d lens at the proximal end, viewing a 1 mm (diameter) square wave grating (8 cycles) on translucent paper at the distal end (see FIG. 9). The tubes were positioned by the subject on the face-plate of a safety mask so that the gratings viewed by each eye were orthogonal in orientation and viewed.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appendant claims.

The invention claimed is:

1. A method for diagnosis of a mood disorder in a test subject, said method including the steps of:
   (a) determining binocular rivalry rate in the subject; and
   (b) comparing said rivalry rate with a corresponding reference rivalry rate to diagnose presence or absence of the mood disorder or predisposition therefor.

2. The method of claim 1 wherein the binocular rivalry rate is measured by:
   (a) displaying an image to the test subject, which image invokes perceptual alternation;
   (b) signalling respective incidences of perceptual alternation in the test subject during a predetermined period to provide a number of signals; and
   (c) dividing the number of signals by the predetermined period to provide the rate of binocular rivalry.

3. The method of claim 2 further characterised by the step of processing each of the signals relating to interhemispheric alternation to convert these signals into digitised signals, and storing the digitised signals for subsequent use.

4. The method of claim 1 wherein presence of the mood disorder is diagnosed, or a predisposition therefor is suggested, when the binocular rivalry rate of the subject is equal to a corresponding reference binocular rivalry rate associated with the mood disorder.

5. The method of claim 1 wherein absence of the mood disorder is diagnosed, or predisposition therefor discounted, when the binocular rivalry rate of the subject is not equal to a corresponding reference binocular rivalry rate associated with the mood disorder, and/or when the binocular rivalry rate of the subject is equal to a corresponding reference binocular rivalry rate associated with normal or control phenotype.

6. The method of claim 4 wherein presence of bipolar disorder is diagnosed, or a predisposition therefor is suggested, when the rate of perceptual alternation in the subject is less than 0.40 Hz.

7. The method of claim 4 wherein presence of bipolar disorder is diagnosed, or a predisposition therefor is suggested, when the rate of perceptual alternation in the subject is less than 0.40 Hz, wherein a stimulus for binocular rivalry comprises moving gratings.

8. The method of claim 4 wherein presence of bipolar disorder is diagnosed, or a predisposition therefor is suggested, when the rate of perceptual alternation in the subject is less than 0.35 Hz.

9. The method of claim 4 wherein presence of bipolar disorder is diagnosed, or a predisposition therefor is suggested, when the rate of perceptual alternation in the subject is less than 0.35 Hz, wherein a stimulus for binocular rivalry comprises moving gratings.

10. The method of claim 4 wherein presence of bipolar disorder is diagnosed, or a predisposition therefor is suggested, when the rate of perceptual alternation in the subject is less than 0.30 Hz.

11. The method of claim 4 wherein presence of bipolar disorder is diagnosed, or a predisposition therefor is suggested, when the rate of perceptual alternation in the subject is less than 0.30 Hz, wherein a stimulus for binocular rivalry comprises moving gratings.

12. The method of claim 5 wherein absence of bipolar disorder is diagnosed, or a predisposition therefor discounted, when the rate of perceptual alternation is greater than 0.40 Hz.

13. The method of claim 5 wherein absence of bipolar disorder is diagnosed, or a predisposition therefor discounted, when the rate of perceptual alternation is greater than 0.40 Hz, wherein a stimulus for binocular rivalry comprises moving gratings.

14. The method of claim 5 wherein absence of bipolar disorder is diagnosed, or a predisposition therefor discounted, when the rate of perceptual alternation is greater than 0.45 Hz.

15. The method of claim 5 wherein absence of bipolar disorder is diagnosed, or a predisposition therefor discounted, when the rate of perceptual alternation is greater than 0.45 Hz, wherein a stimulus for binocular rivalry comprises moving gratings.

16. The method of claim 5 wherein absence of bipolar disorder is diagnosed, or a predisposition therefor discounted, when the rate of perceptual alternation is greater than 0.50 Hz.

17. The method of claim 5 wherein absence of bipolar disorder is diagnosed, or a predisposition therefor discounted, when the rate of perceptual alternation is greater than 0.50 Hz, wherein a stimulus for binocular rivalry comprises moving gratings.

18. The method of claim 4 wherein presence of unipolar disorder is diagnosed, or a predisposition therefor suggested, when the rate of perceptual alternation in the subject is in the range of between 0.35 Hz and 0.45 Hz.

19. The method of claim 4 wherein presence of unipolar disorder is diagnosed, or a predisposition therefor suggested, when the rate of perceptual alternation in the subject is in the range of between 0.35 Hz and 0.45 Hz, wherein a stimulus for binocular rivalry comprises moving gratings.

20. A process for identifying one or more genetic markers associated with a mood disorder, said process including the steps of:
   (a) testing respective members of one or more pedigrees affected by the mood disorder using the method in claim 1;
   (b) identifying members having the mood disorder or predisposition therefor; and
   (c) conducting genetic linkage analysis on the identified members to identify said one or more genetic markers associated with the mood disorder.

21. The process of claim 20 wherein the mood disorder is bipolar disorder.

22. The process of claim 20 wherein the mood disorder is unipolar disorder.

23. A method for assessing the clinical state of a test subject with a mood disorder, said method including the step of comparing measurements of current relative hemispheric activation to corresponding measurements obtained when said subject was euthymic to thereby ascertain the clinical state wherein the relative hemisphere activation is measured by:
   (a) recording binocular rivalry in the test subject;
   (b) calculating a ratio of total time spent perceiving left eye's present image versus right eye's present image;
   (c) determining which eye's presented image is represented in which hemisphere; and
   (d) interpreting which hemisphere has greater relative activation from the results of steps (a) to (c).

24. The method of claim 23 wherein step (c) is characterised by the steps of:
   (a) stimulating one of said hemispheres;
   (b) calculating a post-stimulation ratio of total time spent perceiving left eye's presented image versus right eye's present image; and
   (c) comparing pre- and post-stimulation ratios to determine whether left eye's presented image or right eye's presented image is represented in said stimulated or opposite hemisphere.

25. The method of claim 23 wherein step (c) is characterised by the steps of:
   (a) stimulating one of said hemispheres;
   (b) calculating a post-stimulation ratio of total time spent perceiving left eye's presented image versus right eye's present image; and
   (c) comparing pre- and post-stimulation ratios to determine whether left eye's presented image or right eye's presented image is represented in said stimulated or opposite hemisphere.
   wherein step (a) is characterised in that said stimulation is effected by unilateral caloric vestibular and/or unilateral transcranial magnetic stimulation.

26. A process for identifying one or more genetic markers associated with a mood disorder, said process including the steps of:
   (a) testing respective members of one or more pedigrees affected by the mood disorder using the method of claim 23;
   (b) identifying members having the mood disorder or predisposition thereof; and
   (c) conducting genetic linkage analysis on the identified members to identify said one or more genetic markers associated with the mood disorder.

27. The process of claim 26 wherein the mood disorder is bipolar disorder.

28. The process of claim 26 wherein the mood disorder is unipolar disorder.

* * * * *

UNITED STATES PATENT AND TRADEMARK OFFICE
CERTIFICATE OF CORRECTION

PATENT NO. : 7,115,099 B2
APPLICATION NO. : 10/651516
DATED : October 3, 2006
INVENTOR(S) : Steven Mark Miller et al.

It is certified that error appears in the above-identified patent and that said Letters Patent is hereby corrected as shown below:

Column 1,
Line 23, delete "mama" and insert --mania--.
Line 24, delete "wood" and insert --mood--.
Line 36, delete "fill" and insert --full--.
Line 40, delete "10841091" and insert --1084-1091--.
Line 66, delete "alterations" and insert --alternations--.

Column 5,
Line 8, after "still yet" delete "a".

Column 6,
Line 14, delete "grater" and insert --greater--.

Column 8,
Line 30, delete "mediate" and insert --immediate--.

Column 14,
Line 11, delete "fiat" and insert --first--.

Column 15,
Line 16, delete "drag" and insert --drug--.

Column 17,
Line 27, delete "60 s" and insert --60s--.
Line 49, delete "lest" and insert --test--.

Column 21,
Line 1, delete "(n)" and insert --(n=6)--.
Line 1, after "rates" delete "," (comma).

Column 22,
Line 49, delete "#unrelieved" and insert -- unrelieved--.

Column 23,
Line 2, delete "depression#ie." and insert --depression - ie.--.
Line 3, delete "whet" and insert --when--.

Column 26,
Line 58, delete "eye-f" and insert --eye-of--.
Line 66, delete "(z)" and insert --(Hz)--.

UNITED STATES PATENT AND TRADEMARK OFFICE
CERTIFICATE OF CORRECTION

PATENT NO. : 7,115,099 B2
APPLICATION NO. : 10/651516
DATED : October 3, 2006
INVENTOR(S) : Steven Mark Miller et al.

It is certified that error appears in the above-identified patent and that said Letters Patent is hereby corrected as shown below:

<u>Column 31,</u>
Line 2, delete "7.20" and insert --7.20°--.
Line 41, delete "50 d" and insert --50d--.

Signed and Sealed this

Thirteenth Day of March, 2007

JON W. DUDAS
*Director of the United States Patent and Trademark Office*